(12) United States Patent
Sadeghi et al.

(10) Patent No.: US 11,024,406 B2
(45) Date of Patent: Jun. 1, 2021

(54) SYSTEMS AND METHODS FOR IDENTIFYING ERRORS AND/OR CRITICAL RESULTS IN MEDICAL REPORTS

(71) Applicant: Nuance Communications, Inc., Burlington, MA (US)

(72) Inventors: Sepehr Sadeghi, Lexington, MA (US); Atul T. Mistry, North Andover, MA (US)

(73) Assignee: Nuance Communications, Inc., Burlington, MA (US)

( * ) Notice: Subject to any disclaimer, the term of this patent is extended or adjusted under 35 U.S.C. 154(b) by 0 days.

(21) Appl. No.: 13/795,741

(22) Filed: Mar. 12, 2013

(65) Prior Publication Data

US 2014/0278448 A1    Sep. 18, 2014

(51) Int. Cl.
*G16H 15/00* (2018.01)
*G06F 40/237* (2020.01)
*G16H 40/67* (2018.01)

(52) U.S. Cl.
CPC ........... *G16H 15/00* (2018.01); *G06F 40/237* (2020.01); *G16H 40/67* (2018.01)

(58) Field of Classification Search
CPC .......... G06Q 50/22–24; G06F 19/3487; G06F 17/27; G16F 17/27; G16H 15/00
See application file for complete search history.

(56) References Cited

U.S. PATENT DOCUMENTS

| | | | |
|---|---|---|---|
| 4,696,039 A | 9/1987 | Doddington | |
| 5,031,113 A | 7/1991 | Hollerbauer | |
| 5,051,924 A | 9/1991 | Bergeron et al. | |
| 5,664,109 A | 9/1997 | Johnson et al. | |
| 5,680,511 A | 10/1997 | Baker et al. | |
| 5,758,322 A | 5/1998 | Rongley | |
| 5,787,394 A | 7/1998 | Bahl et al. | |
| 5,909,667 A | 6/1999 | Leontiades et al. | |
| 5,999,896 A | 12/1999 | Richardson et al. | |
| 6,003,002 A | 12/1999 | Netsch | |
| 6,073,101 A | 6/2000 | Maes | |

(Continued)

FOREIGN PATENT DOCUMENTS

| | | |
|---|---|---|
| DE | 19533541 C1 | 3/1997 |
| EP | 2 169 577 A1 | 3/2010 |

(Continued)

OTHER PUBLICATIONS

U.S. Appl. No. 11/322,971, Zimmerman et al., filed Dec. 30, 2005.

(Continued)

*Primary Examiner* — Sheetal R Paulson

(74) *Attorney, Agent, or Firm* — Wolf, Greenfield & Sacks, P.C.

(57) ABSTRACT

Systems and methods for analyzing a medical report to determine whether the medical report includes at least one instance of at least one category selected from a group consisting of: gender error, laterality error, and critical finding. In some embodiments, one or more portions of text are identified from the medical report. Contextual information associated with the medical report is used to determine whether the identified one or more portions of text comprise at least one instance of at least one category selected from the group.

21 Claims, 18 Drawing Sheets

(56) References Cited

U.S. PATENT DOCUMENTS

| | | | |
|---|---|---|---|
| 6,122,613 | A | 9/2000 | Baker |
| 6,173,259 | B1 | 1/2001 | Bijl et al. |
| 6,212,498 | B1 | 4/2001 | Sherwood et al. |
| 6,304,848 | B1 | 10/2001 | Singer |
| 6,308,158 | B1 | 10/2001 | Kuhnen et al. |
| 6,360,237 | B1 | 3/2002 | Schulz et al. |
| 6,366,882 | B1 | 4/2002 | Bijl et al. |
| 6,418,410 | B1 | 7/2002 | Nassiff et al. |
| 6,434,547 | B1 | 8/2002 | Mishelevich et al. |
| 6,463,413 | B1 | 10/2002 | Applebaum et al. |
| 6,487,530 | B1 | 11/2002 | Lin et al. |
| 6,567,778 | B1 | 5/2003 | Chao Chang et al. |
| 6,813,603 | B1 | 11/2004 | Groner et al. |
| 6,999,933 | B2 | 2/2006 | Hoi |
| 7,289,825 | B2 | 10/2007 | Fors et al. |
| 7,379,946 | B2 | 5/2008 | Carus et al. |
| 7,383,172 | B1 | 6/2008 | Jamieson |
| 7,493,253 | B1 | 2/2009 | Ceusters et al. |
| 7,610,192 | B1* | 10/2009 | Jamieson ............... G06Q 40/08 704/9 |
| 8,117,034 | B2 | 2/2012 | Gschwendtner |
| 8,364,499 | B2* | 1/2013 | Maughan ............... G16H 40/20 705/2 |
| 8,694,335 | B2 | 4/2014 | Yegnanarayanan |
| 8,738,403 | B2 | 5/2014 | Flanagan et al. |
| 9,478,218 | B2 | 10/2016 | Shu |
| 9,564,126 | B2 | 2/2017 | Ganong, III et al. |
| 9,818,398 | B2 | 11/2017 | Ganong, III et al. |
| 2003/0115083 | A1 | 6/2003 | Masarie, Jr. et al. |
| 2005/0033574 | A1 | 2/2005 | Kim et al. |
| 2005/0114140 | A1 | 5/2005 | Brackett et al. |
| 2006/0041428 | A1 | 2/2006 | Fritisch et al. |
| 2007/0033026 | A1 | 2/2007 | Bartosik et al. |
| 2007/0106508 | A1 | 5/2007 | Khan et al. |
| 2007/0208567 | A1 | 9/2007 | Amento et al. |
| 2007/0260977 | A1 | 11/2007 | Allard et al. |
| 2007/0299651 | A1 | 12/2007 | Koll et al. |
| 2008/0228769 | A1 | 9/2008 | Lita et al. |
| 2008/0255835 | A1 | 10/2008 | Ollason et al. |
| 2010/0049756 | A1 | 2/2010 | Chemitiganti et al. |
| 2010/0094657 | A1 | 4/2010 | Stern et al. |
| 2010/0114597 | A1 | 5/2010 | Shreiber et al. |
| 2010/0114598 | A1 | 5/2010 | Oez |
| 2010/0324927 | A1 | 12/2010 | Tinsley |
| 2010/0324936 | A1 | 12/2010 | Vishnubhatla et al. |
| 2012/0166225 | A1 | 6/2012 | Albro et al. |
| 2012/0212337 | A1 | 8/2012 | Montyne et al. |
| 2012/0221347 | A1* | 8/2012 | Reiner .................. G06Q 10/00 705/2 |
| 2012/0226719 | A1* | 9/2012 | Sewall ..................... 707/803 |
| 2019/0046126 | A1 | 2/2019 | Owen et al. |
| 2019/0051376 | A1 | 2/2019 | Gallopyn et al. |
| 2019/0051377 | A1 | 2/2019 | Owen et al. |
| 2019/0051381 | A1 | 2/2019 | Owen |
| 2019/0066821 | A1 | 2/2019 | Owen et al. |

FOREIGN PATENT DOCUMENTS

| | | |
|---|---|---|
| EP | 2 235 654 A1 | 10/2010 |
| WO | WO 98/19253 A1 | 5/1998 |
| WO | WO 2009/081306 A1 | 7/2009 |

OTHER PUBLICATIONS

Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine Learning Methods, Bonn, Germany, (2005).

Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.

Florian et al., "A Statistical Model for Multilingual Entity Detection and Tracking," Proceedings of the Human Language Technologies Conference 2004 (HLT-NAACL'04), (2004).

Gomez-Perez et al., "An overview of methods and tools for ontology learning from texts," Knowledge Engineering Review 19:3 p. 187-212, 2004.

Salton et al., "A Vector Space Model for Automatic Indexing," Communications of the ACM, vol. 18, No. 11, Nov. 1975.

Welty et al., "Large Scale Relation Detection," Proceedings of the NAACL HLT 2010 First International Workshop on Formalisms and Methodology for Learning by Reading, pp. 24-33, Los Angeles, California, Jun. 2010.

International Search Report and Written Opinion for PCT/US2014/019385 dated Aug. 4, 2014.

[No Author Listed] "Montage Healthcare Signals a New Direction in Radiology Quality". Montage Healthcare Solutions. Press Release. Philadelphia. Nov. 15, 2012. Available at http://montagehealthcare.com/press-releases/2012-11-15-montage-healthcare-signals-a-new-direction-in-radiology-quality/.

Carestream Health, "Montage Signal at RSNA 2012." CareStream Health. YouTube. Dec. 4, 2012. Available at http://www.youtube.com/watch?v=_s3Pnb0f3ZA. Retrieved on Jul. 17, 2014.

Sangwaiya et al., Errare Humanum Est: Frequency of Laterality Errors in Radiology Reports. American Journal of Roentgenology. 2009;192: W239-W244.

Aronow et al., Ad Hoc Classification of Radiology Reports. Journal of the American Medical Informatics Association. 1999;6(5):393-411.

Bateman et al., The Quest for the Last 5%: Interfaces for Correcting Real-Time Speech-Generated Subtitles. Interactive Posters. CHI 2000. 2 pages.

Birnbaum et al., Report: A Voice Password System for Access Security. AT&T Technical Journal. 1986. 7 pages.

Bisani et al., Automatic Editing in a Back-End Speech-to-Text System. Proceedings of ACL-08: HLT. 2008:114-20.

Heng-Hsou et al., An Event-Driven and Ontology-Based Approach for the Delivery and Information Extraction of E-mails. IEEE. 2000. 103-9.

Hewitt et al., Real-Time Speech-Generated Subtitles: Problems and Solutions. ISCA Archive. 6th International Conference on Spoken Language Processing (ICSLP 2000). 2000. 5 pages.

Mendonca et al., Extracting information on pnemonia in infants using natural language processing of radiology reports. Journal of Biomedical Informatics. 2005;38:314-21.

Naik, Speaker Verification: A Tutorial. IEEE Communications Magazine. 1990:42-8.

Newman et al., Speaker Verifcation Through Large Vocabulary Continuous Speech Recognition. Dragon Systems, Inc. 1996. 4 pages.

Rosenberg, Evaluation of an Automatic Speaker-Verification System Over Telephone Lines. Manuscript received Sep. 9, 1975. The Bell System Technical Journal. 1976;55(6):723-44.

Shvaiko et al., Ontology Matching OM-2008. Papers from the ISWC Workshop. 2008. 271 pages.

Sistrom et al., Managing Predefined Templated and Macros for a Departmental Speech Recognition System Using Common Software. Journal of Digital Imaging. 2001;14(3):131-41.

Soderland et al., Automated Classification of Encounter Notes in a Computer Based Medical Record. MEDINFO 1995 Proceedings. 1995 IMIA. 9 pages.

Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.

Sonntag et al., RadSpeech's Mobile Dialogue System for Radiologists. IUI'12. 2012. 2 pages.

Suhm, Multimodal Interactive Error Recovery for Non-Conversation Speech User Interfaces. Dissertation. 1998. 292 pages.

Taira et al., Automatic Structuring of Radiology Free-Text Reports. infoRAD. Radiology 2001;21:237-45.

(56) References Cited

OTHER PUBLICATIONS

Chang et al., Non-Clinical Errors Using Voice Recognition Dictation Software for Radiology Reports: A Retrospective Audit. J Digit Imaging. 2011;24:724-8.
Cooper et al., Chapter 9. Orchestration and Flow. About Face 2.0—The Essentials of Interaction Design. 2003. 43 pages.
Duda et al., Chapter 1. Introcution. Pattern Classification. 2001. 2d Eds. 32 pages.
Norman, The Design of Everyday Things. Basic Books. 1988. pp. 99-101, 177-179, 197-200.
Voll, A Methodology of Error Detection: Improving Speech Recognition in Radiology. Thesis Submitted in Partial Fulfillment of the Requirements for the Degree of Doctor of Philosophy. Simon Fraser University. Spring 2006. 208 pages.

\* cited by examiner

Exam: MR <u>arthrogram</u> of the <u>right shoulder</u> [2014-06-17]

A405 *Laterality Of* A410 — *Subject Of* — A400

History: Right shoulder pain status post injury. Rule out biceps tendon injury/labral tear.

Comparison: Right shoulder radiographs [2014-03-16]

*Laterality Of* A420 — *Subject Of*

Technique: Following <u>left shoulder arthrogram</u>, multiplanar T1 and T2-weighted MR images were obtained.
A415

Findings: Bone marrow signal intensity is within normal limits. Benign 8mm bone island is present in the proximal right humerus. No fracture or dislocation. No labral tear. Mild supraspinatus, infraspinatus and biceps tendinosis. Subscapularis tendon appears normal. Cartilage intact.

Impression:
1. No labral tear.
2. Biceps tendinosis but no tear.
3. Supraspinatus and infraspinatus tendinosis.

FIG. 4

*Laterality Of*

Right hip 2 views: [2014-06-17].

History: Ortho followup.

Priors: Comparison to [2014-04-15].

*Subject Of*

Findings: A total hip arthroplasty has been performed. The hip is in relative anatomic position and alignment. The osseous structures are intact. The relationship between the osseous structures and the prosthetic components is unremarkable and unchanged  Soft tissue ossification is noted lateral to the hip which is increased since [2014-03-27]. There are mild degenerative changes of the left hip.

*Laterality Of*

Conclusion: Left THA.  No significant change, except for increase in soft tissue ossification.

SYSTEMS AND METHODS FOR IDENTIFYING ERRORS AND/OR CRITICAL RESULTS IN MEDICAL REPORTS

BACKGROUND

1. Field

The techniques described herein are directed generally to the field of medical documentation, and more particularly to techniques for creating and processing patient records in medical settings.

2. Description of the Related Art

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff, test results, treatments received, and/or plans for future treatment. Such documentation helps to maintain continuity across multiple instances of medical care received by the patient over time. In addition, when an institution's medical records for large numbers of patients are considered in the aggregate, the information contained therein can be useful for many purposes, such as educating clinicians (e.g., with respect to treatment efficacy and best practices), internal auditing within the institution, quality assurance, etc.

Historically, each patient's medical record was maintained as a physical paper folder, often referred to as a "medical chart," or "chart". Each patient's chart would include a stack of paper reports, such as intake forms, history and immunization records, laboratory results, and clinicians' notes. Following an encounter with the patient (e.g., an office visit, a hospital round, or a surgical procedure), a clinician conducting the encounter would provide a narrative note about the encounter to be included in the patient's chart. Such a note could include, for example, a description of the reason(s) for the patient encounter, an account of any vital signs, test results, and/or other clinical data collected during the encounter, one or more diagnoses determined by the clinician from the encounter, and/or a description of a plan for further treatment.

Medical professionals other than clinicians may also provide narrative notes to be included in patients' charts. For example, a radiologist may analyze information obtained from an imaging study and generate a medical report that includes the radiologist's impressions. Such impressions may include, for example, the radiologist's interpretations of one or more medical images (e.g., one or more diagnoses) and/or notes for possible follow-up tests, procedures, and/or treatments.

Often, a medical professional would dictate a note into an audio recording device or a telephone giving access to such a recording device. Later, a medical transcriptionist would listen to the audio recording and transcribe it into text, which could be printed on paper and inserted into the patient's chart for future reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's date of birth, gender, medical history, etc. Electronic medical records can also be shared, accessed, and updated by multiple different persons locally and from remote locations through suitable user interfaces and network connections, eliminating the need to retrieve and deliver paper files from a crowded file room.

SUMMARY

In accordance with some embodiments, a system is provided, comprising at least one processor and at least one storage medium storing executable instructions, the at least one processor being programmed by the executable instructions to analyze a medical report to determine whether the medical report includes at least one instance of at least one category selected from a group consisting of: gender error, laterality error, and critical finding, wherein analyzing the medical report comprises acts of: identifying, from the medical report, one or more portions of text; and using contextual information associated with the medical report to determine whether the one or more portions of text comprise at least one instance of at least one category selected from the group.

In accordance with some further embodiments, a method is provided, comprising using at least one processor to analyze a medical report to determine whether the medical report includes at least one instance of at least one category selected from a group consisting of: gender error, laterality error, and critical finding, wherein analyzing the medical report comprises acts of: identifying, from the medical report, one or more portions of text; and using contextual information associated with the medical report to determine whether the one or more portions of text comprise at least one instance of at least one category selected from the group.

In accordance with some further embodiments, at least one computer-readable storage medium is provided, having stored thereon instructions that, when executed by at least one processor, perform a method comprising using at least one processor to analyze a medical report to determine whether the medical report includes at least one instance of at least one category selected from a group consisting of: gender error, laterality error, and critical finding, wherein analyzing the medical report comprises acts of: identifying, from the medical report, one or more portions of text; and using contextual information associated with the medical report to determine whether the one or more portions of text comprise at least one instance of at least one category selected from the group.

BRIEF DESCRIPTION OF DRAWINGS

In the drawings:

FIG. 2 shows an illustrative user interface A200 for creating and/or reviewing medical reports, in accordance with some embodiments;

FIG. 3 shows the illustrative user interface A200 of FIG. 2, with a popup window 300 to notify a user that one or more alerts have been triggered during a quality assurance check, in accordance with some embodiments;

FIG. 4 shows an illustrative report text A400 in which a laterality error may be identified using one or more natural language understanding (NLU) techniques, in accordance with some embodiments;

FIG. 5 shows another illustrative report text A500 in which a laterality error may be identified using one or more NLU techniques, in accordance with some embodiments;

FIG. 9 shows an illustrative graphical user interface for a medical fact review system, in accordance with some embodiments;

FIG. 10A shows an illustrative display of medical facts in a user interface, in accordance with some embodiments;

FIG. 10B shows another illustrative display of medical facts in a user interface, in accordance with some embodiments;

FIG. 11 shows an illustrative display of linkage between text and a clinical fact, in accordance with some embodiments;

DETAILED DESCRIPTION

Figure 1:
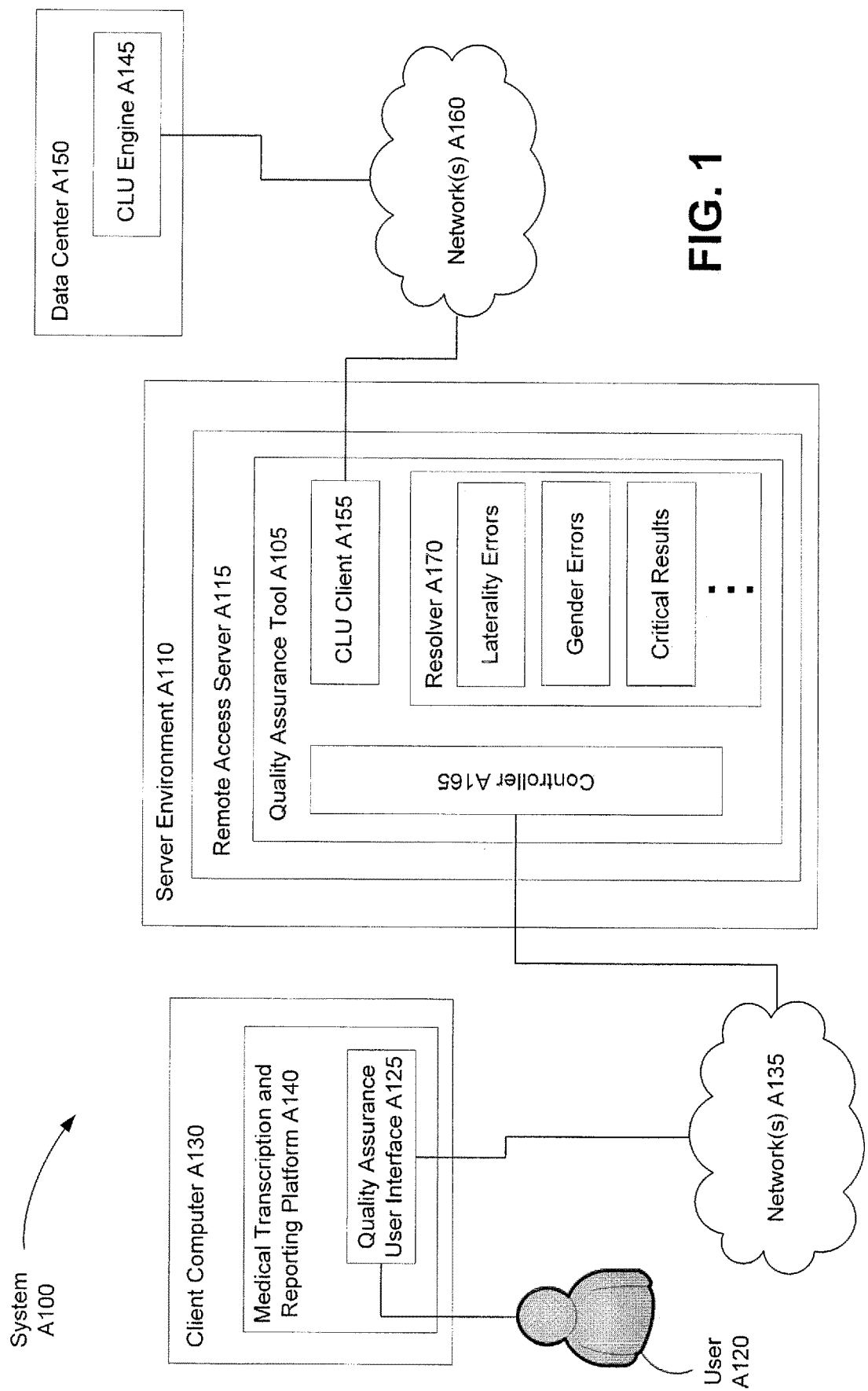
FIG. 1 shows an illustrative system A100 in which a quality assurance tool may be used to process medical reports, in accordance with some embodiments.

The inventors have recognized and appreciated that many medical professionals may prefer to enter medical data by providing a free-form note, rather than using a data-entry interface that requires a user to navigate through different screens, menus, text fields, checkboxes, radio buttons, etc. Medical professionals may also prefer to use medical terms of their own choice, as opposed to being confined to a set of standard terms (e.g., as imposed by a certain organization or institution).

Moreover, medical professionals may prefer to dictate a note because speaking can often be faster than typing. For instance, dictation allows a radiologist to provide his impressions as he is viewing one or more medical images, without having to switch his visual attention to another physical or virtual screen to type or click.

Whether by speaking or typing, free-form narration allows medical professionals to be unconstrained in what they say and how they say it. However, the inventors have recognized and appreciated that such freedom may result in human errors. For example, a medical professional preparing a note regarding an examination or study of a patient's left leg may, somewhere in the note, refer instead to the patient's lower right extremity. Such errors are referred to herein as "laterality" errors. These errors are easy to overlook even if the medical professionals review their reports prior to submission. The inventors have recognized and appreciated that identifying and correcting laterality errors may improve safety and efficiency in the delivery of healthcare, for example, by reducing the need to investigate and correct a medical report long after it was created (when the medical professional who created the report no longer remembers details relating to the report), by preventing a medical procedure from being performed on the wrong part of a patient's body, etc. Additionally, accurate reporting may reduce opportunities for insurance companies to reject claims, so that health care providers may be compensated in a more timely fashion.

The inventors have recognized and appreciated that gender errors may also occur in medical reports. Examples of gender errors include, but are not limited to, pronoun mismatches (e.g., "he" vs. "she"), anatomy mismatches (e.g., the existence of a prostate in a female study), and pathology mismatches (e.g., ovarian cancer for a male patient). These errors may occur for various reasons. For example, a radiologist may simply be looking at images for a male patient X while dictating into a female patient Y's medical report. The inventors have recognized and appreciated that catching such errors at an early stage (e.g., before the author of a report finalizes and submits the report) may allow the errors to be corrected much more efficiently, because the relevant information (e.g., medical images, lab results, etc.) may still be readily available and/or fresh in the author's mind.

The inventors have also recognized and appreciated that the timely identification of, and response to, medical conditions that require immediate attention may be important. For example, a medical report (e.g., a radiologist's report) may include one or more phrases (e.g., "hemorrhage of the brain") that suggest a dangerous condition. If the report were to go through regular processing, the ordering clinician may not be notified in time to act upon the dangerous condition. Furthermore, a critical result may be buried deep in a medical report among descriptions of other issues and may escape the clinician's attention. Further still, a critical result may not be apparent unless multiple facts in a medical report are analyzed collectively, but such facts may be scattered throughout the report so that the critical result may be missed.

Accordingly, the inventors have recognized and appreciated that it may be beneficial to automatically analyze medical reports to identify critical results during, or soon after, the generation of the reports. If critical results are identified, alerts may be provide to some appropriate personnel. For example, in some embodiments, an alert may be provided to a radiologist when he reviews a report he just dictated, before he "signs off" and submits the report for delivery to the ordering clinician.

The inventors have further recognized and appreciated that a high rate of false positives (i.e., generating an alert for an error or critical result where the alleged error or critical result does not exist) may negatively impact user experience and discourage medical professionals from adopting a system that automatically checks for errors and critical results in medical reports. For instance, because dealing with false positive alerts takes time, medical professionals may be unwilling to adopt a system that generates a high rate of false positives, or may simply ignore the alerts. Accordingly, the inventors have recognized and appreciated that it may be beneficial to minimize the occurrence rate of false positive alerts.

To illustrate how false positive alerts may occur, consider, for example, the following report text.

Mammography of the right breast shows no signs of malignancy.

Left breast used as comparison.

This text recites both "right breast" and "left breast." An alert suggesting a laterality error would be a false positive, however, because the left breast was studied and discussed for comparison purposes, even though the study was ordered for the right breast.

As discussed below, in accordance with some embodiments, contextual information (e.g., the presence of the word "comparison" in proximity to the reference to the left breast) is used to distinguish a legitimate reference from an erroneous one and thereby reduce false positives.

As another example, consider the following report text.

There is no indication of tension pneumothorax.

If "tension pneumothorax" is recognized as a critical result, a critical result alert generated for this text would be a false positive because of the negation in the text, "no indication." Again, in accordance with some embodiments discussed below, the use of contextual information may reduce false positives.

The inventors have recognized and appreciated that one or more natural language understanding (NLU) techniques may be employed to analyze one or more portions of text in a medical report to identify certain errors and/or critical results. Such techniques may use contextual information to evaluate words in the identified text and determine whether that the identified text represents an error or critical result.

Any suitable contextual information or combination thereof may be used to understand the analyzed text (which may reduce the occurrence rate of false positive alerts), as aspects of the present disclosure are not limited to the use of any particular type or combination of contextual information. The proximal presence of the word "comparison" in the first report text discussed above and the negative context created by the phrase "no indication" in the second report text discussed above are non-limiting examples of contextual information that can be used to understand the other text in the report (e.g., "left breast" and "tension pneumothorax," respectively, in the examples above) and determine whether that an error or critical result has been identified. In some embodiments, information that is not part of the report text, such as metadata associated with the medical report, may also be used. Non-limiting examples of metadata include patient gender (e.g., male, female, unknown, unspecified, etc.), order procedural description (e.g., "XRAY Left Leg," "Left," "L," "Right," "Rt," "R," etc.), order procedure code (e.g., as established by a medical institution, insurance company, government agency, or other organization), etc.

It should be appreciated that the term "medical report" as used herein is not limited to final reports (e.g., those ready to be included in patient health records). A medical report may be raw text transcribed from audio and/or other information that is not yet a finished product ready to be included in a patient health record.

In some embodiments, the techniques employed for detecting errors and/or critical results may include one or more techniques for detecting and/or tracking mentions of entities (i.e., things) in a report text. For example, with respect to the illustrative mammography report text discussed above, the phrase "right breast" may be a mention of an entity, namely, the patient's right breast. The phrase "left breast" may be a mention of a different entity, namely, the patient's left breast. However, if the author of the report made a laterality error, the phrases "right breast" and "left breast" are references in the report text to the same entity (i.e., the patient's right breast), but with one reference misidentifying the entity. Thus, one or more entity detection and/or tracking techniques may be used to determine whether two or more references refer to the same entity but using inconsistent identifiers for it, for example, by determining whether the phrase "left breast" in the example above is a mention of the patient's left breast (in which case there is no laterality error) or a mention of the patient's right breast (in which case there is a laterality error).

In some embodiments, the techniques employed to detect errors and/or critical results may include one or more statistical techniques. For example, one or more statistical models may be trained using a corpus of medical reports that are hand-annotated with labels indicative of errors (e.g., laterality and/or gender errors) and/or critical results. Such statistical models capture the likelihoods of various patterns observed in the training corpus, and may be used to determine the likelihood that one or more given portions of text in a particular medical report represents an error or critical result. For example, with respect to the illustrative mammography report text discussed above, there may be a non-zero probability that the phrase "left breast" is a laterality error, because it has the characteristic of being found in a sentence immediately following a sentence containing the phrase "right breast." However, another characteristic of the phrase "left breast," namely, that it occurs in the proximity of the word "comparison," may lower the probability of the phrase "left breast" actually being a laterality error.

As discussed above, the inventors have recognized and appreciated that it may be beneficial to provide alerts to medical professionals when errors and/or critical results are identified in medical reports. In some embodiments, a user-friendly interface is provided that allows the medical professionals to review and/or validate the alerts efficiently. For example, a user reviewing a medical report (e.g., a radiologist reviewing a report that he just dictated or is in the process of dictating) may be presented with one or more alerts. In some embodiments, the alerts may be organized according to their types (e.g., laterality errors, gender errors, critical results, etc.), but the techniques described herein are not limited to organizing alerts this way or another way.

In some embodiments, upon the user selecting a particular alert, the user may be presented with further information relating to that alert. For example, in some embodiments, the one or more portions of text in the report that triggered the alert may be presented to the user. To facilitate the user's review, such triggering text may be presented within the context of some surrounding text, but with one or more visual indications (e.g., highlighting, different color of text, different font, flashing icons, etc.) to show the user where the triggering text is located. Other ways of presenting alerts to a user may also be used and are discussed in greater detail below.

While providing further information to the user may be advantageous, not all embodiments are so limited. In alternative embodiments, the system may simply present an alert and rely on the user to determine why the alert arose.

In some further embodiments, the system may allow a user to explicitly resolve an alert, for example, by accepting or rejecting it. The user may accept the alert if after reviewing the associated information the user believes the error or critical condition does exist. Alternatively, the user may reject the alert if after reviewing the associated information the user believes that the alert is a false positive. For example, the user may determine that the one or more portions of text that triggered an alert contains a legitimate reference to an entity of an opposite laterality or gender (e.g., "left breast" being referenced for comparison purposes in the mammography example above). As another example, the user may determine that, while a dangerous condition is referenced, the context in which it occurs does not suggest a need for immediate action (e.g., the reference to "tension pneumothorax" in a negative context in the example above). As yet another example, the user may determine that no opposite laterality or gender or dangerous condition is referenced at all in the report text.

If the user accepts the alert, the system may further allow the user to take an appropriate action, for example, by making a correction in the report. Depending on institutional policy, the user may in some instances be required to resolve certain ones or all of the alerts. For example, a radiologist creating a report may be required to resolve, or at least acknowledge, every alert before he is able to "sign off" on the report.

The inventors have recognized and appreciated that the information provided by a user in resolving an alert may be used to improve the system's ability to accurately identify errors and/or critical results. For example, in an embodiment in which a statistical model is used to generate alerts, a user's feedback (e.g., acceptance or rejection of an alert) may be used as additional training data to adapt the statistical model. Thus, adaptation may be performed continually as the system is being used. However, not all embodiments are limited to adapting the system.

While a number of inventive features are described herein for creating and/or processing medical reports, it should be appreciated that embodiments of the present disclosure may include any one of these features, any combination of two or more features, or all of the features, as aspects of the present disclosure are not limited to any particular number or combination of the features described herein. The aspects of the present disclosure described herein can be implemented in any of numerous ways, and are not limited to any particular implementation techniques. Described below are examples of specific implementation techniques; however, it should be appreciate that these examples are provided merely for purposes of illustration, and that other implementations are possible.

One illustrative application of the techniques described herein is a quality assurance (QA) tool for use in processing medical reports. FIG. 1 shows an illustrative system A100 in which such a QA tool may be used, in accordance with some embodiments. In this example, the system A100 includes multiple computers configured to communicate with each other via one or more networks. It should be appreciated that such an arrangement is merely illustrative, as other arrangements may also be suitable. For example, all of the functionalities described herein in connection with the system A100 may be implemented on a single computer, as opposed to being distributed over multiple computers. Furthermore, the processing tasks described herein may be distributed over multiple computers in any suitable way, as aspects of the present disclosure are not limited to any particular distribution of processing tasks.

In the example of FIG. 1, a QA tool A105 is implemented as a process that is running in a server environment A110 and can be accessed through a remote access server A115. The remote access server A115 may handle various tasks (e.g., authentication) to allow a user A120 to access the QA tool A105 from a QA user interface A125. The remote access server A115 may use any suitable remote access protocol or combination of such protocols, as aspects of the present disclosure are not limited to any particular way of accessing the QA tool A105.

In the example of FIG. 1, the QA user interface A125 runs on a client computer A130 that is located remotely from the server environment A110 and is configured to communicate with the server environment A110 through one or more networks A135. However, it should be appreciated that in alternative embodiments the QA user interface A125 may run on a computer that is on the same local area network as the server environment A110, or may run on the same hardware as the server environment A110.

In some embodiments, the QA tool A105 may be provided to the user A120 as part of a bundle of capabilities related to creating and processing medical reports. For example, an automatic transcription service (not shown) may be provided to perform automatic speech recognition (ASR) processing on audio signals captured from the user A120. This may allow the user A120 to dictate a medical report or one or more portions thereof and then submit the transcribed text to the QA tool A105 for further processing such as checking for errors and/or critical results. However, it should be appreciated that aspects of the present disclosure are not limited to the use of ASR in creating medical reports. A report may be generated in any suitable way, such as by typing, pointing-and-clicking, and/or handwriting (e.g., via automatic handwriting recognition).

In some further embodiments, the QA tool A105 may be integrated with one or more other processes related to creating and processing medical reports (e.g., automatic transcription) to provide a seamless user experience. This may be accomplished by providing access to these processes via a single platform, such as the medical transcription and reporting platform A140 shown in FIG. 1. However, it should be appreciated that aspects of the present disclosure are not limited to the use of a unified platform, as the QA tool A105 may alternatively be provided as a stand-alone process.

As discussed above, the inventors have recognized and appreciated that one or more NLU techniques may be used to identify errors (e.g., laterality and/or gender errors) and/or critical results in medical reports. Again, the techniques described herein may be applied to any suitable types of medical reports, including finished reports ready to be included in patient medical records and/or reports that are still work in progress.

Accordingly, in some embodiments, the QA tool A105 may invoke a NLU engine to process the medical reports to be quality assured. The NLU engine may be built and/or tuned using information specific to the medical field. Non-limiting examples of such information include a lexicon of medical terms, an ontology linked to medical terms, a medical knowledge representation model, a statistical entity detection model trained using hand-annotated medical documents, and/or a statistical relation model similarly trained. Such an NLU engine is sometimes referred to herein as a clinical language understanding (CLU) engine. Various illustrative ways to implement a CLU engine are described in greater detail below.

Although expert knowledge in the medical field may enhance the system's ability to correctly identify errors and/or critical results, it should be appreciated that not every component of a CLU engine may incorporate such knowledge. In various embodiments, one or more components of a CLU engine may be generic (i.e., not specific to the medical field). On the other hand, one or more components of a CLU engine may incorporate knowledge from one or more subfields within the medical field. Thus, a CLU engine may be built and/or tuned using domain knowledge at any suitable level of specificity, as aspects of the present disclosure are not limited to any particular way of building and/or tuning a CLU engine.

In the example shown in FIG. 1, the QA tool A105 uses a CLU engine A145 to identify errors and/or critical results in medical reports. In this embodiment, the CLU engine A145 is implemented as a process running at a data center A150, which may be a cloud computing facility or some other type of facility that is capable of performing computational tasks associated with the CLU engine A145. The QA tool A105 may use a CLU client A155 to access the CLU engine A145 via one or more networks A160.

In some embodiments, the QA tool A105 may operate in real time. For example, in some embodiments, the QA tool A105 may check a medical report as soon as the report text becomes available and/or before the author "signs" the report. As used herein, "signing" is an act performed by an author of a report (e.g., a clinician or lab technician) to indicate the report is ready to be made part of a patient's medical record. Depending on the particular implementation, this act may or may not include the author attaching an electronic signature to the report, and the electronic signature may or may not be a cryptographic signature. Furthermore, the author may sign the report before the report is complete, and may supplement the report with additional information at a later time.

While the CLU engine A145 runs at a data center in some embodiments, such an arrangement is not required. The CLU engine A145 may in alternative embodiments execute within the server environment A110 or on the client computer A130. Also, the QA tool A105 need not operate in real time. For example, in alternative embodiments, the QA tool A105 may process medical reports offline (e.g., in batches).

In some embodiments, the QA tool A105 may receive the report text to be processed from the client computer A130. For example, the QA tool A105 may receive the report text from the QA user interface A125 or some other component of the medical transcription and reporting platform A140. In an embodiment in which an ASR engine (not shown) is used to transcribe a dictated note into text, the QA tool A105 may receive the report text directly from the ASR engine.

In the example shown in FIG. 1, a controller component A165 of the QA tool A105 may interact with the QA user interface A125 to receive medical reports to be processed and/or to return processing results. Upon receiving a medical report from the QA user interface A125 or some other source, the controller A165 may extract certain data from the report, such as the text to be checked and/or any desired combination of metadata that may be used to inform the CLU engine's analysis. Non-limiting examples of metadata include patient gender, order procedure code (e.g., as established by a medical institution, insurance company, government agency, or other organization), order procedural description (e.g., "XRAY Left Leg"), etc. The extracted data may then be passed to the CLU client A155 to be submitted to the CLU engine A145 for analysis.

In some embodiments, the CLU client A155 may forward output received from the CLU engine A145 to a resolver component A170 of the QA Tool A105 for further processing. The resolver A170 may be programmed to parse the output of the CLU engine A145, which may be in any suitable format (e.g., an XML format such as a Clinical Document Architecture (CDA) format), and identify any errors and/or critical results of interest to the resolver A170.

In one embodiment, the resolver A170 may apply one or more rules to the CLU engine output to determine whether the CLU engine output includes any errors and/or critical results of interest. For example, a rule may search the CLU engine output for an extracted fact of "laterality mismatch" type, "gender mismatch" type, "critical result" type, etc. The rules may take any form and may depend on the format of the CLU engine output. Additionally, the resolver A170 may be used when the CLU engine A145 also extracts facts of types other than those of interest. In such embodiments, the resolver A170 may determine which, if any, of the extracted facts is of interest to the resolver A170.

It should be appreciated that not all embodiments are limited to the use of a resolver. For example, in alternative embodiments, a CLU engine may directly provide alerts for errors and/or critical results.

If one or more rules are triggered, the resolver A170 may generate one or more alerts accordingly. In some embodiments, the resolver A170 may send these alerts, either directly or via the controller A165, to the QA user interface A125 to be displayed to the user A120. It should be appreciated that the user A120 may, although need not, be the author of the report that was checked by the QA tool A105.

While some details of implementation are described above in connection with FIG. 1, it should be appreciated that such details are provided solely for purposes of illustration. The concepts described above may be implemented in other ways, for example, without the use of the remote access server A115. For example, in alternative embodiments, the QA tool A105 may execute on a local computer, may execute remotely and be accessed via a web interface, or in any other suitable way. Additionally, aspects of the present disclosure are not limited to the use of a CLU client for accessing a CLU engine, as the CLU engine may be invoked in any suitable way.

Figure 2:
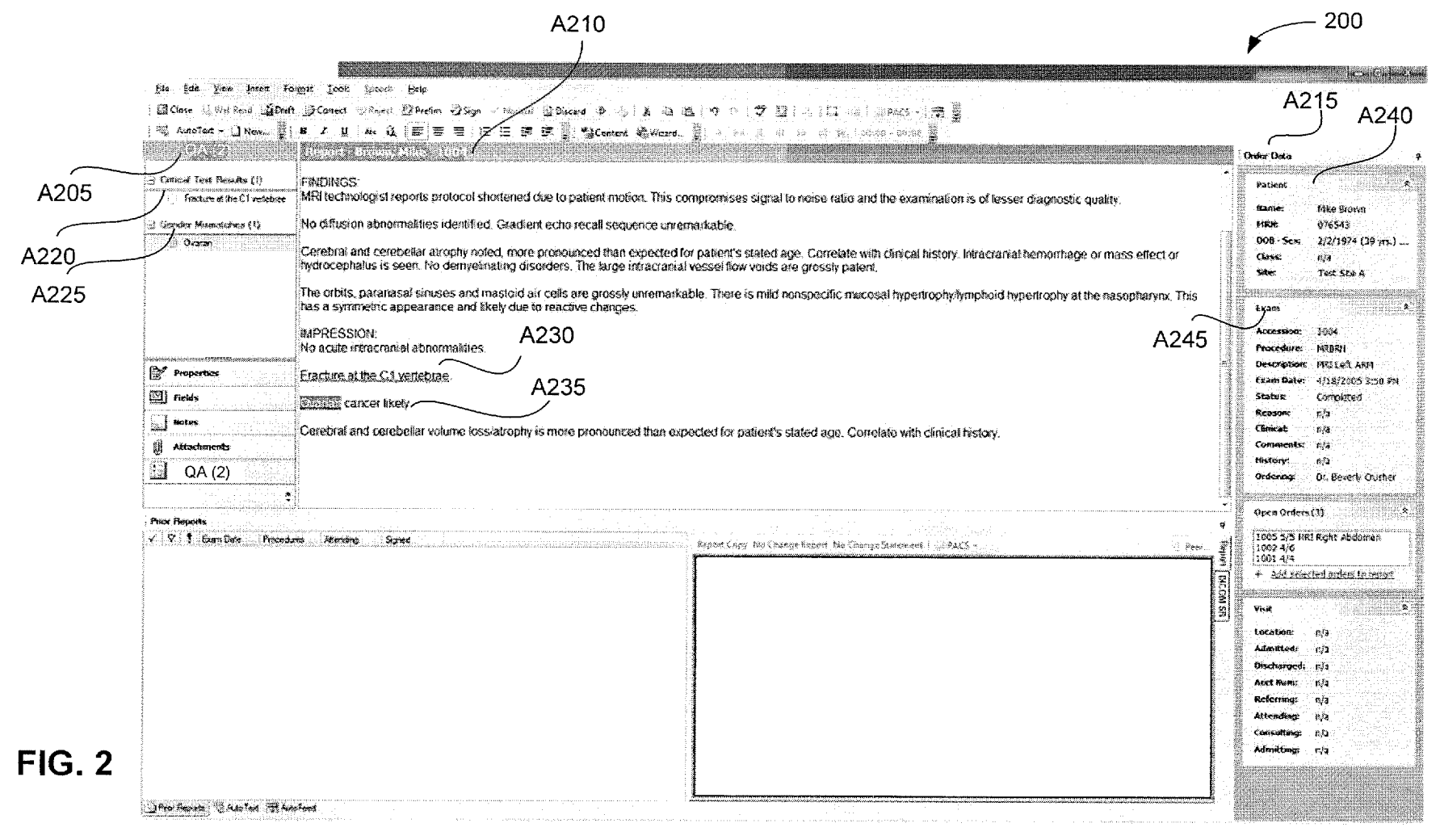

FIG. 2 shows an illustrative user interface A200 for creating and/or reviewing medical reports, in accordance with some embodiments. In this example, the user interface A200 is a unified interface for interacting with various processes accessible through a platform, such as the medical transcription and reporting platform A140 shown in FIG. 1 and discussed above. Each accessible process may be associated with one or more panes in the user interface A200. For instance, a QA tool (e.g., the QA tool A105 shown in FIG. 1 and discussed above) may be associated with a QA pane A205 through which a user may interact with the QA tool. However, it should be appreciated that in alternative embodiments a QA tool may not be integrated with other processes and may have an independent user interface.

In the example of FIG. 2, the user interface A200 includes additional panes, such as a "Report" pane A210 and an "Order Data" pane A215. The Report pane A210 may display the text of a medical report for a user's review and/or edit. The Order Data pane A215 may display one or more pieces of metadata associated with the medical report displayed in the Report pane A210.

As discussed above, in some embodiments, alerts may be organized according to their types, for example, laterality errors, gender errors, critical results, etc. As shown in FIG. 2, the QA pane A205 indicates that in this particular example two types of alerts have been generated, critical results and gender errors. A critical results section A220 may show the total number of critical results identified (e.g., "1") and list each such critical result (e.g., "fracture at the C1 vertebrae"). A gender error section A225 may show the total number of gender errors identified (e.g., "1") and list each such gender error (e.g., "ovarian" for a male patient).

In the example shown in FIG. 2, the simultaneous display of the QA pane A205 and the Report pane A210 may allow a user to determine efficiently whether the system has correctly identified an error or critical result with respect to an alert. In some embodiments, the report text may be displayed in the Report pane A210 in such a manner as to differentiate one or more portions of text that triggered an alert. This may allow the user to quickly identify where triggering text is located in the medical report. For example, the text "Fracture at the C1 vertebrae" (shown at A230 in FIG. 2) may be underlined, whereas the text "Ovarian" (shown at A235 in FIG. 2) may be highlighted. Other suitable visual indications (e.g., different colors of highlighting/text, different fonts, icons, etc.) or combinations thereof may also be used. For example, a different color of highlighting in the text may be associated with each alert (e.g., yellow for "fracture at the C1 vertebrae," orange for "ovarian," etc.), so that the user can quickly determine which portion(s) of text correspond to which alert. As another example, a different color of highlighting in the text may be associated with each type of alert (e.g., yellow for critical results, orange for gender errors, etc.), so that the user can quickly determine which portion(s) of text correspond to which type of alert.

Displaying the entire report text with the triggering text highlighted or otherwise visually differentiated may allow the user to take advantage of the context of the report in assessing whether each alert indeed corresponds to an error or critical result. In some embodiments, the entire text is displayed. However, in alternative embodiments, only one or more portions of the text may be displayed. For example, the triggering text corresponding to an alert may be displayed with a suitable amount of surrounding text (e.g., one, two, or three sentences, a certain number of words preceding and/or following the triggering text, etc.), which may provide sufficient context to allow the user to evaluate an alert.

In the example shown in FIG. 2, the simultaneous display of the QA pane A205 and the Order Data pane A215 may also facilitate a user's review of alerts. As discussed above, the Order Data pane A215 may display metadata associated with the medical report displayed in the Report pane A210. In some embodiments, the Order Data pane A215 may include a "Patient" subpane A240 that displays information regarding the patient who is the subject of the medical report displayed in the Report pane A210. Any suitable patient information may be displayed, including, but not limited to, name, medical record number (MRN), date of birth, age, sex, class (e.g., a patient classification assigned by a medical institution), site (e.g., where the patient received the examination discussed in the medical report), etc.

Using the information displayed in the Patient subpane A240, the user may be able to efficiently determine whether the system has correctly identified an error or critical result with respect to an alert. For example, upon seeing the gender error "ovarian" shown in the QA pane A205, the user may quickly check the Patient subpane A240 and see that the patient is male, so "ovarian" would represent a gender error. The user may also confirm by reviewing the text in the Report pane A210 and determine that the comment "Ovarian cancer likely" in the "IMPRESSIONS" section does not make sense for a male patient.

Having satisfied himself that an alert is legitimate, the user may wish to take one or more appropriate actions. In some embodiments, the user may directly edit the report text in the Report pane A210. For example, if the user is the author of the report and is in the process of reviewing the report prior to signing, the user may determine that "Ovarian cancer likely" is a speech recognition error and may still remember what he intended to put into the report instead of "Ovarian cancer likely." In the case of a radiology report, the radiologist may still have the relevant images on his screen and be able to review one or more images when correcting an error in the report. These are merely examples, as the user may edit the report in any suitable way. In these examples, the alerts are generated in real time, which facilitates efficient correction by the user. However, as stated above, not all embodiments are limited to real time alerts.

In some further embodiments, the user may notify an appropriate party in addition to, or instead of, correcting the report. For example, if the user is a QA person reviewing a report after it has been signed, the user may notify the author of the report and request that the report be corrected. Additionally, or alternatively, the user may notify the ordering clinician, so that the ordering clinician can determine as quickly as possible whether any further remedial actions are warranted. In the event of a critical result alert, the user may also notify emergency personnel to attempt to contact and/or locate the patient.

Returning to FIG. 2, the Order Data pane A215 may in some further embodiments include an "Exam" subpane A245 that displays information regarding the examination discussed in the medical report displayed in the Report pane A210. Non-limiting examples of examination information include accession number (which may be unique for the particular instance of the examination conducted), procedure code, procedure description, date and time, status, reason for conducting the examination, related clinical data, comments (e.g., from an ordering clinician), patient medical history, identity of the ordering clinician, etc. Any of this information may assist the user in determining whether the system has correctly identified an error or critical result with respect to an alert (e.g., by providing an indication of the laterality of an anatomical feature to which the text displayed in the Report pane A210 relates).

While particular pieces of information are shown in FIG. 2 in a particular arrangement, it should be appreciated that aspects of the present disclosure are not limited to any particular way of displaying information to the user. Other combinations and/or arrangements of information may also be displayed. For example, in some embodiments, the combination and/or arrangement of displayed information may be user configurable, so that different medical professionals (e.g., a radiologist vs. a clinician conducting a patient encounter) may customize the user interface to suit their particular needs.

In some embodiments, quality assurance checks may be automatically performed as part of a medical report generation workflow. For example, a check may be invoked automatically when the author indicates he wishes to "sign" the report. Alternatively, or additionally, the author may manually invoke a check at any time, including before he is ready to "sign" the report.

Figure 3:
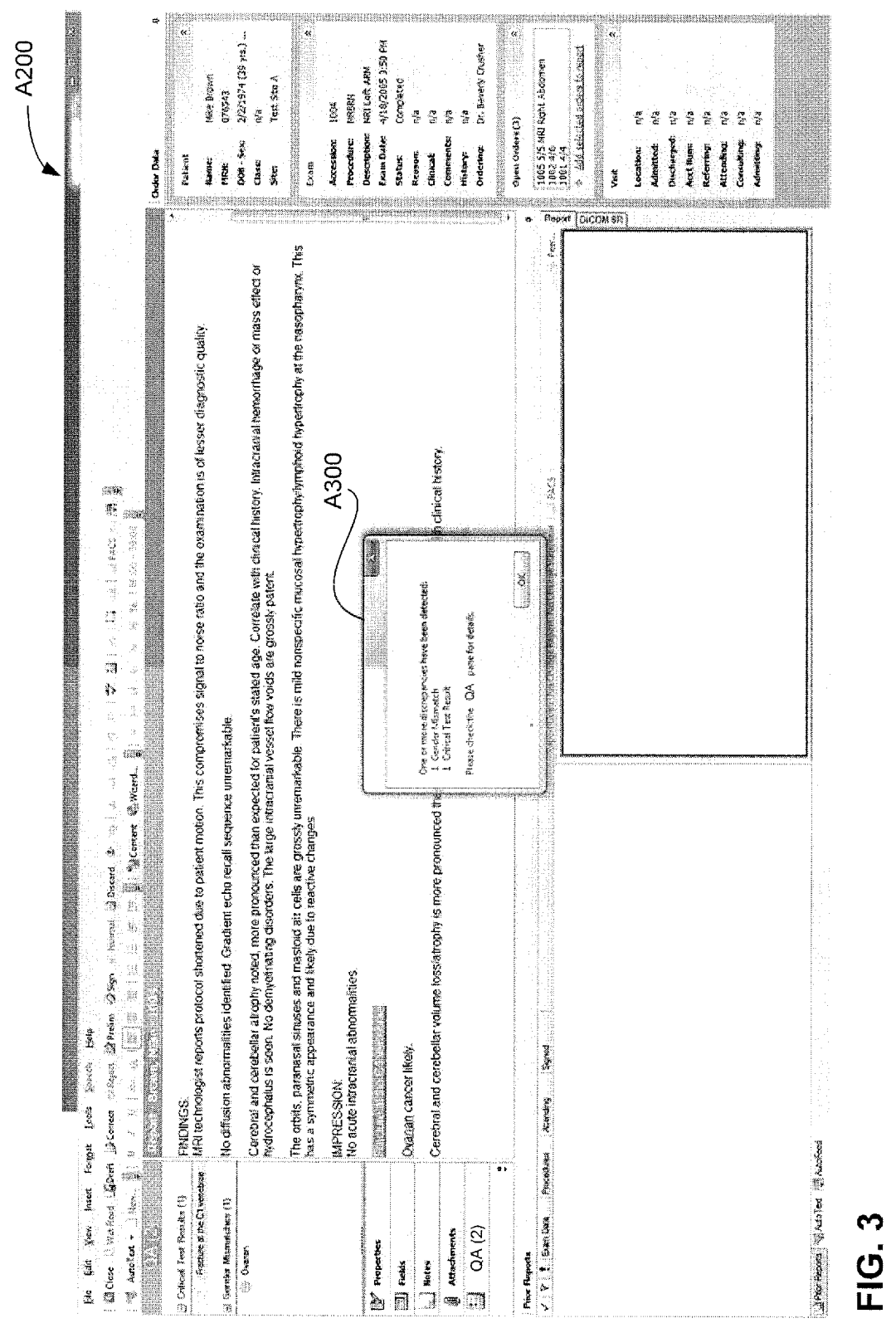

FIG. 3 shows the illustrative user interface A200 of FIG. 2, with a popup window A300 to notify a user that one or more alerts have been triggered during a quality assurance check, in accordance with some embodiments. In this example, the popup window identifies the types of alerts generated and the number of alerts for each such type (e.g., "1 Gender Mismatch" and "1 Critical Test Result") and prompts the user to refer to the QA pane A205 for details. In alternative embodiments, a notification may simply indicate that at least one alert has been generated, without identifying any type or number. Other ways of notifying the user may also be possible, as aspects of the present disclosure are not limited to any particular manner of notification. For example, a flashing icon, a scrolling banner, and/or an audible and/or tactile alert may be used rather than, or in addition to, a popup window.

FIG. 4 shows an illustrative report text A400 in which a laterality error may be identified using one or more NLU techniques, in accordance with some embodiments. For example, the techniques described in connection with FIG. 4 may be used by the illustrative CLU engine A145 shown in FIG. 1 and discussed above to process the report text A400.

In this example, the report text A400 discusses a magnetic resonance anthrogram of a patient's shoulder. At A405, in the "Exam" section, the report recites "anthrogram." At A410, also in the "Exam" section, the report recites "right shoulder." At 415, in the "Technique" section, the report recites "left shoulder anthrogram."

In some embodiments, occurrences of the word "shoulder" may be annotated (e.g., by the CLU engine A145 in the example of FIG. 1) with the entity type label "Anatomical Feature" (not shown), and occurrences of the word "anthrogram" may be annotated with the entity type label "Study" (not shown). Similarly, occurrences of the words "left" and "right" may be annotated (e.g., by the CLU engine A145 in the example of FIG. 1) with the entity type label "Laterality" (not shown). Because both "left" and "right" have multiple senses (e.g., "right" can mean "correct" or refer the side of a person that points to the east when the person faces north, and "left" can be the past participle of the verb "leave" or refer the side of a person that points to the west when the person faces north), one or more word sense disambiguation techniques (e.g., using deterministic rules and/or statistical models trained using hand-annotated data) may be used to determine whether each occurrence of "right" or "left" should be labeled "Laterality."

Returning to FIG. 4, the word "right" at A410 and the immediately following word "shoulder" may be annotated with a relation label "Laterality Of," indicating that the word "right" specifies the laterality of the entity denoted by the word "shoulder" at A410. Similarly, at A415, the word "left" and the immediately following word "shoulder" may be annotated with a relation label "Laterality Of," indicating that the word "left" specifies the laterality of the entity denoted by the word "shoulder" at A415. Additionally, at A410 and A405, the word "shoulder" and the non-contiguously preceding word "anthrogram" may be annotated with a relation label "Subject Of," indicating that the entity denoted by the word "shoulder" (which is an anatomical feature) is the subject of the entity denoted by the word "anthrogram" (which is a study performed on an anatomical feature).

The annotation of terms and/or tuples of terms with appropriate labels may be done in any suitable manner, for example, by a CLU engine using deterministic rules and/or statistical models. The deterministic rules may be designed by experts with knowledge of the medical field in general and/or one or more relevant subfield(s). The statistical models may be trained using any suitable corpus of medical documents, which may be generic or specific to one or more subfields. Examples of techniques that can be applied by a CLU engine to annotate an input text are described in greater detail below.

In some embodiments, one or more entity tracking techniques may be applied to determine that the occurrence of the word "anthrogram" at A405 and the occurrence of the same word at A420 are likely to be mentions of the same entity. Examples of entity detection and/or tracking techniques are described in greater detail below.

In some embodiments, if the occurrence of the word "anthrogram" at 405 and the occurrence of the same word at A420 are mentions of the same entity, an inference may be drawn that the occurrence of the word "shoulder" at A410 and the occurrence of the same word at A415 are also likely to be mentions of the same entity, because they stand in the same relation (i.e., "Subject Of") with "anthrogram" at A405 and "anthrogram" at A420, respectively, as illustrated below:

"shoulder" at A410 is "Subject Of" "anthrogram" at A405 AND

"shoulder" at A415 is "Subject Of" "anthrogram" at A420.

This type of inference may be made in any suitable way, for example, by a CLU engine using deterministic rules and/or statistical models trained using hand-annotated data. For example, in an embodiment in which one or more statistical models are used, it may be observed from the training data that if each of X and Y is related to Z by the same relation "Subject Of," there is a certain likelihood that X and Y refer to the same entity. If that observed likelihood is sufficiently high (e.g., above a selected threshold), the CLU engine may conclude that X and Y refer to the same entity whenever the same pattern (i.e., each of X and Y is related to Z by the relation "Subject Of,") is found in an input text.

If the occurrence of the word "shoulder" at A410 and the occurrence of the same word at A415 are mentions of the same entity, then an inconsistency may be deemed to exist by the CLU engine because the laterality of that entity is both "left" (based on the "Laterality Of" label at A410) and "right" (based on the "Laterality Of" label at A415), and a laterality error may be identified by the CLU engine accordingly.

While examples of inference making techniques are discussed above, it should be appreciated that aspects of the present disclosure are not limited to the use of such techniques, as a CLU engine may use any suitable technique or combination of techniques to detect errors and/or critical results.

FIG. 5 shows another illustrative report text A500 in which a laterality error may be identified using one or more NLU techniques (e.g., by the CLU engine A145 in the example of FIG. 1), in accordance with some embodiments. In this example, the report text 500 discusses an imaging study of a patient's hip. At A505, the report recites "Right hip." At A510, in the "Findings" section, the report recites "total hip anthroplasty." At A515, also in the "Findings" section, the report recites "hip." At A520, in the "Conclusion" section, the report recites "Left THA."

As discussed above, an ontology linked to medical terms may be used by a CLU engine in some embodiments and may facilitate identifying errors and/or critical results in a medical report. For instance, with respect to the example shown in FIG. 5, an ontology may indicate that the two terms "total hip antroplasty" and "THA" refer to the same concept in the ontology. Accordingly, both terms may be annotated by the CLU engine with the same entity type label "Procedure" (not shown), indicating that each of them is a mention of an entity of the type "Procedure." Examples of ontologies are described in greater detail below.

Returning to the example shown in FIG. 5, occurrences of the word "hip" may be annotated with the entity type label "Anatomical Feature" (not shown), and occurrences of the words "left" and "right" may be annotated with the entity type label "Laterality" (not shown). Additionally, the word "Right" at A505 and the immediately following word "hip" may be annotated with a relation label "Laterality Of," indicating that the word "Right" specifies the laterality of the entity denoted by the word "hip." Similarly, at A520, the word "Left" and the immediately following word "THA" may be annotated with a relation label "Laterality Of," indicating that the word "Left" specifies the laterality of the entity denoted by the word "THA." Lastly, at A510 and A515, the word "hip" and the non-contiguously preceding phrase "total hip anthroplasty" may be annotated with a relation label "Subject Of," indicating that the entity denoted by the word "hip" (which is an anatomical feature) is the subject of the entity denoted by the phrase "total hip anthroplasty" (which is a procedure performed on an anatomical feature).

Once the report text A500 has been annotated, the CLU engine may draw one or more inferences, for example, using deterministic rules and/or statistical models. For example, one or more entity tracking techniques may be applied to determine that the occurrence of the word "hip" at A505 and the occurrence of the same word at A515 are likely to be mentions of the same entity. This may allow an inference that the laterality of the entity denoted by the word "hip" at A515 is also "Right," so that a new relation label "Laterality Of" (not shown) may be added to the word "Right" at A505 and the word "hip" at A515. This new label, combined with the existing "Subject of" label from A515 to A510, may further allow the following inference and yet another new label, namely, "Laterality Of" from A505 to A510 (not shown):

"Right" is "Laterality Of" "hip"
AND
"hip" is "Subject Of" "total hip anthroplasty"
IMPLIES
"Right" is "Laterality Of" "total hip anthroplasty."

Additionally, one or more entity tracking techniques may be applied to determine that the term "total hip anthroplasty" at A510 and the term "THA" at A520 are also likely to be mentions of the same entity. This may be deemed by the CLU engine to be an inconsistency because the laterality of that entity is both "Left" (based on the existing "Laterality Of" label at A520) and "Right" (based on the inferred "Laterality Of" label above), and a laterality error may be identified by the CLU engine accordingly.

While various NLU techniques are discussed above in connection with the examples shown in FIGS. 4-5, it should be appreciated that aspects of the present disclosure are not limited to the use of any particular NLU technique or combination of NLU techniques. Any of the NLU techniques discussed herein may be used alone or in combination with one or more other NLU techniques in identifying errors and/or critical results in medical reports. Additionally, although in the examples of FIGS. 4-5 the CLU engine analyzes an input text to identify errors and/or critical results, not all embodiments are limited to the analysis being performed by the CLU engine. In alternative embodiments, some or all of the analysis may be performed by some other component of the system (e.g., the resolver A170 in the example of FIG. 1), or collectively by multiple components.

Figure 6:
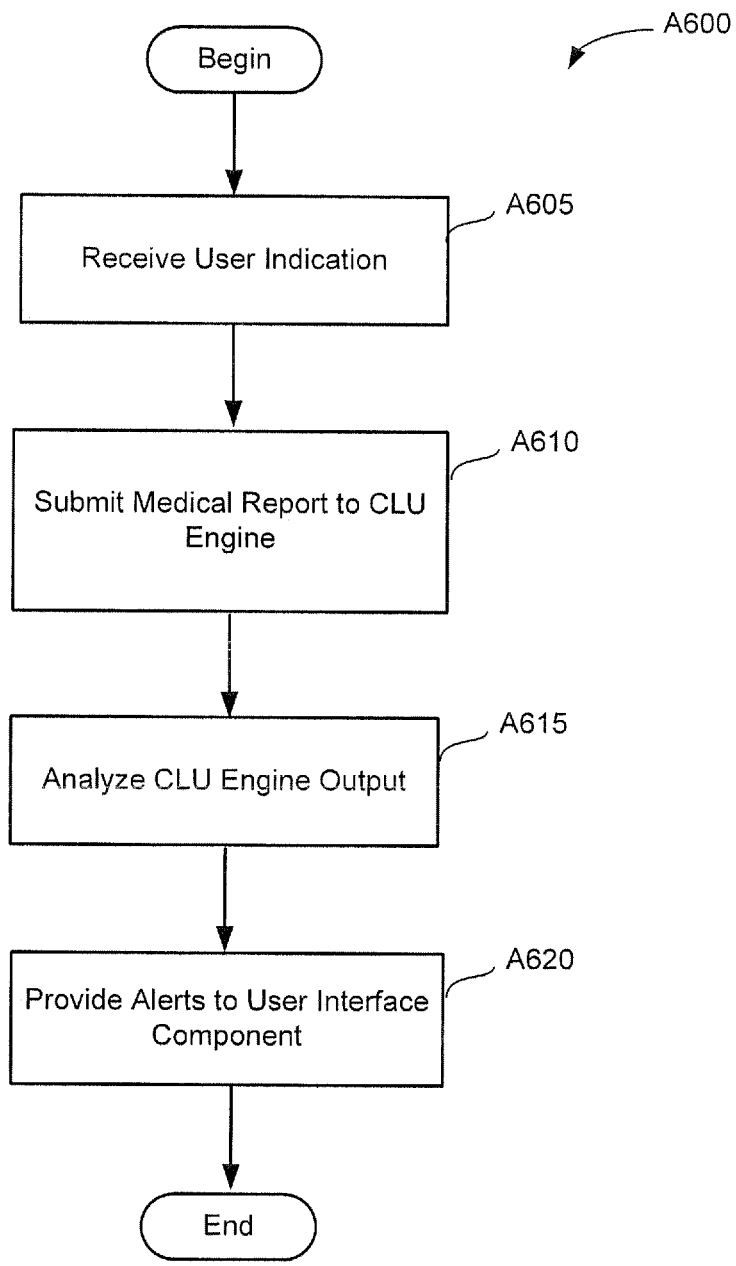
FIG. 6 shows an illustrative process A600 that may be performed to identify errors and/or critical results in medical reports, in accordance with some embodiments.

FIG. 6 shows an illustrative process A600 that may be performed to identify errors and/or critical results in medical reports, in accordance with some embodiments. For example, the process A600 may be performed by the illustrative QA tool A105 shown in FIG. 1 and discussed above.

In the example shown in FIG. 6, an indication may be received from a user at act A605. As discussed above, the indication may be an explicit request to initiate quality assurance checking on one or more medical reports, an indication that the user is ready to "sign" one or more medical reports, or any other type of indication that may trigger a quality assurance check, as aspects of the present disclosure are not limited to the examples discussed herein.

At act A610, one or more medical reports (or one or more portions thereof) to be quality assured may be submitted to a CLU engine for processing. The CLU engine may be built and/or adapted to identify errors (e.g., laterality and/or gender errors) and/or critical results using any one or combination of the techniques described herein. Furthermore, in some embodiments, one or more pieces of metadata (e.g., patient gender, order procedure code, order procedural description, etc.) may be submitted to the CLU engine along with report text to supply additional contextual information. However, it should be appreciated that not all embodiments are limited to the use of metadata as contextual information in identifying errors and/or critical results. In some embodiments, the CLU engine may evaluate one or more portions of text in a medical report using, as contextual information, other text in the report.

At act A615, one or more outputs of the CLU engine may be analyzed. As discussed above, an output of the CLU engine may be in any suitable format, non-limiting examples of which include markup language formats such as a Clinical Documentation Architecture (CDA) format or some other XML format. Accordingly, in some embodiments, analyzing an output of the CLU engine may include parsing the output according to parsing rules associated with the particular format expected from the CLU engine.

In further embodiments, analyzing the output of the CLU engine may include applying one or more rules that perform functions in addition to parsing the CLU engine output. For example, there may be a set of one or more rules for each type of alert (e.g., laterality error, gender error, or critical result) that the system is capable of generating. The rule sets may be selectively enabled or disabled, so that a user may configure the system to detect different types of errors and/or critical results. For instance, a particular medical institution, department, or user may be interested in receiving only alerts of a selected set of alert types. As a non-limiting example, a broad set of critical result types may be defined by some organizations (e.g., industry association, government agency, insurance company, etc.), but a particular institution (e.g., hospital) may wish to receive alerts for only a selected subset of critical result types. Because the CLU engine may be used to analyze reports for multiple institutions, it may be built and/or tuned to identify all critical result types in the broader set. Therefore, in some embodiments, the processing of the CLU engine output (e.g., by the resolver A170 in the example of FIG. 1) may apply rules to filter out certain types of errors and/or critical results identified by the CLU engine. Depending what the CLU engine is configured to return as output, other types of information may also be filtered out, such as laterality and/or gender matches (as opposed to mismatches).

In an embodiment in which the CLU engine output is a structured document (e.g., in a CDA format), applying a rule may include identifying one or more relevant sections in the document and searching those sections for any indication that the CLU engine identified an error or critical result. As a non-limiting example, an indication that the CLU engine identified an occurrence of "Left" in a study of some "Right" anatomical feature may trigger a laterality mismatch alert.

As another example, an indication that the CLU engine identified an occurrence of "Prostate" in a study of a female patient may trigger a gender mismatch alert. As yet another example, an indication that the CLU engine identified an occurrence of "Tension Pneumothorax" may trigger a critical result alert.

In some embodiments, application of rules may be done while parsing is still on-going. For example, when a particular section in the output has been identified, an appropriate set of rules may be applied while the rest of the output is still being parsed. However, that is not required as the application of rules may in alternative embodiments be performed after parsing has been completed. Also, it should be appreciated that applying a rule may also include searching the entire CLU engine output, without being limited to any particular portion of the output.

Returning to FIG. 6, one or more alerts triggered at act A615 may be provided to a user interface component (e.g., the illustrative QA user interface A125 shown in FIG. 1) at act A620 to be displayed to the user. The alerts may be provided in any suitable form. For example, in some embodiments, an alert may include a corresponding portion of the CLU engine output, which may in turn include one or more portions of report text that were identified by the CLU engine as representing an error or critical result, and/or locations of such text in the report. In other embodiments, an alert may include information regarding a corresponding rule applied to the CLU engine output and how the rule was triggered. Other types of information may also be provided, as aspects of the present disclosure are not limited to any particular combination of information provided to the user interface component.

In some further embodiments, one or more filters may be applied at act A620 to prevent certain alerts from being provided to the user. This may be an alternative way to filter out a selected set of errors and/or critical results identified by the CLU engine, so that alerts based those errors and/or critical results are not generated, as discussed above in connection with act A615.

Figure 7:
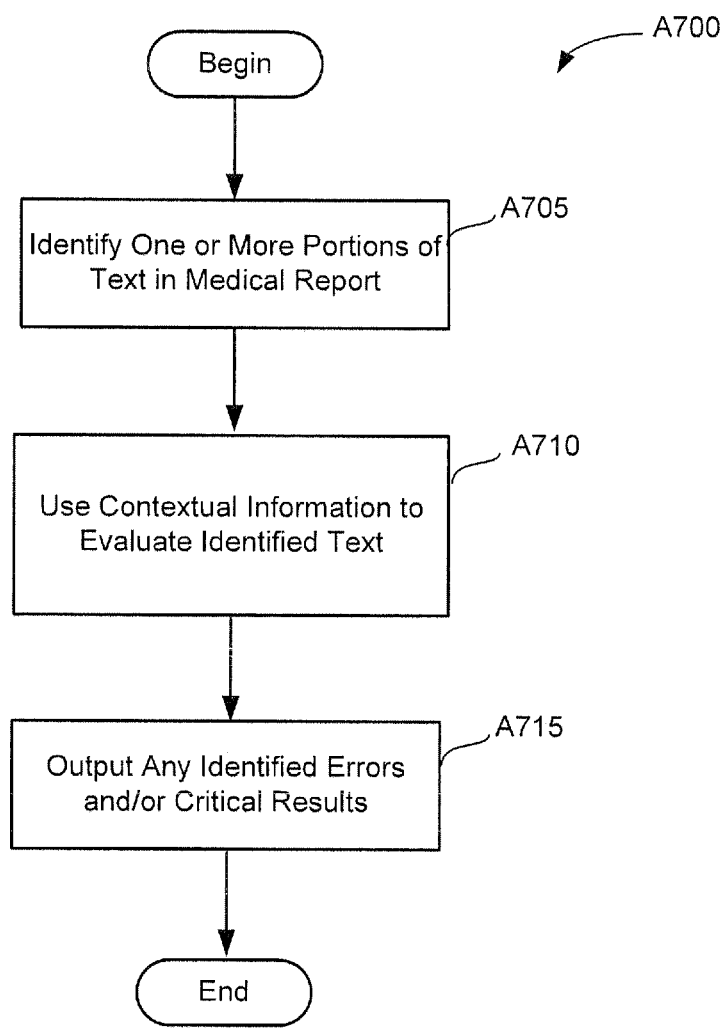
FIG. 7 shows another illustrative process A700 that may be performed to identify errors and/or critical results in medical reports, in accordance with some embodiments.

FIG. 7 shows another illustrative process A700 that may be performed to identify errors and/or critical results in medical reports, in accordance with some embodiments. For example, the process A700 may be performed by the illustrative CLU engine A145 shown in FIG. 1 and discussed above.

At act A705, one or more portions of text may be identified by a CLU engine from an input medical report. In some embodiments, identifying one or more portions of text may be done at least in part using a tokenization process, which may break down the report text into various levels of syntactic substructure, such as words, phrases, etc. Illustrative techniques for tokenization are discussed below in greater detail. However, it should be appreciated that aspects of the present disclosure are not limited to the use of tokenization techniques to identify one or more portions of text to be analyzed, as the CLU engine may do so in any suitable way. For example, in alternative embodiments, the CLU engine may identify one or more portions of text to be analyzed by searching for selected words or phrases (e.g., "left," "right," "ovarian," etc.).

At act A710, the one or more portions of identified text may be analyzed in context to determine whether they include one or more errors and/or critical results. As discussed above, the use of contextual information in determining whether the identified text includes errors and/or critical results may reduce the rate of false positives generated by the system. For example, in some embodiments, the analysis at act A710 may take into account one or more portions of text in the report other than the identified text (e.g., as discussed above in connection with FIGS. 4-5). In further embodiments, the analysis at act A710 may additionally take into account one or more pieces of metadata, such as patient gender as discussed above in connection with FIG. 2.

In an embodiment in which one or more statistical techniques are employed, a confidence value may be computed for a candidate of an error or critical result and may be indicative of how similar this particular candidate is to one or more patterns in the training data that were hand-annotated as errors and/or critical results. A threshold confidence level may be set so that a candidate is flagged as an error or critical result if it is associated with a confidence value above the threshold level. This threshold may be applicable to all types of errors and/or critical results, or a different threshold may be used for each type of errors and/or critical results.

At act A715, the CLU engine may output any identified errors and/or critical results. As discussed above, the identified errors and/or critical results may be packaged into a structured document having a certain format (e.g., a CDA format). For example, the document may have certain sections such as "Laterality," "Gender," "Critical Results," etc. However, it should be appreciated that aspects of the present disclosure are not limited to the use of structured outputs.

In some embodiments, output relating to an identified error or critical result may include the corresponding one or more portions of text and/or locations of such text in the report. When one or more statistical techniques are employed in some embodiments, confidence information may be provided with an identified error or critical result, such as a confidence score as discussed above in connection with act A710. However, not all embodiments are limited to outputting confidence information. Also, other types of information may be included in the output, as aspects of the present disclosure are not limited to any particular combination of information output by a CLU engine.

While illustrative sequences of processing steps are discussed above in connection with FIGS. 6-7, it should be appreciated that aspects of the present disclosure are not limited to the use of any particular workflows or processing steps. All of the tasks described herein relating to identifying errors and/or critical results may be implemented and/or distributed among various system components in any suitable manner.

Below are detailed descriptions of illustrative medical fact extraction techniques that may be used in conjunction with various techniques described above for identifying errors and/or critical results in medical reports, in accordance with some embodiments. For example, techniques for extracting medical facts may be used to identify errors and/or critical results, as discussed above in connection with FIG. 7.

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

While some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present disclosure are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present disclosure are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the present disclosure are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present disclosure are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present disclosure are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely illustrative, as aspects of the present disclosure are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present disclosure are not limited in this respect. Exemplary implementations for a fact extraction component are described in detail below.

Automatic extraction of medical facts (e.g., clinical facts) directly from a free-form narration of a patient encounter provided by a clinician may create the opportunity for numerous enhancements to processes involved in medical documentation in healthcare institutions. Some such enhancements may help make it possible for a clinician to efficiently oversee a process involving deriving any one or combination of updated patient records, billing information, ordering information, quality of care assurances, decision support, etc., directly from a free-form narration in a single interactive session with a medical fact review system.

In some embodiments, automatic extraction of clinical facts from a textual representation of a clinician's free-form narration (e.g., from a text narrative) of a patient encounter may be enhanced by re-formatting the text narrative to facilitate the automatic extraction of the clinical facts. For example, in some embodiments a fact extraction component that performs the automatic fact extraction may make use of linguistic knowledge that has some dependency on accurate placement of sentence boundaries in the text narrative. Accordingly, in some embodiments, the fact extraction may be enhanced by adding, removing and/or correcting sentence boundaries in the text narrative to comply with the linguistic structure expected by the fact extraction component. Examples of ways in which sentence boundary pre-processing can be implemented are described below. In another example, automatic fact extraction may be enhanced by normalizing section headings in the text narrative to comply with standard section headings used by the healthcare institution for which the clinical documentation is being performed.

In some embodiments, a linkage may be maintained between each extracted clinical fact and the portion of the free-form narration from which that fact was extracted. For example, if a fact corresponding to "acute myocardial infarction" is extracted from a free-form narration because it included the term "heart attack", a linkage may be maintained between that extracted fact and the words "heart attack" in the free-form narration. In some embodiments, while the clinician or another user is reviewing the extracted clinical facts via a user interface to a fact review system, the system may provide one or more indicators to the user (who may be the clinician himself or a different person) of the different linkages between the different extracted facts and the portions of the free-form narration from which they were extracted. Such indicators may be visual indicators, audio indicators, or any other suitable type of indicators, as aspects of the present disclosure are not limited in this respect. In some embodiments, such linkage indicators may enhance the ability of the clinician or other user to review the extracted facts for accuracy, with reference to the specific parts of the free-form narration that generated them. In some embodiments, if a textual representation of the free-form narration has been re-formatted prior to fact extraction, linkages may still be maintained between the extracted facts and the original text narrative, to allow the user to relate the extracted facts to the narration as it was originally given by the clinician. While some embodiments provide linkage information for each extracted fact, it should be appreciated that aspects of the present disclosure relating to providing linkage information are not so limited, as linkage information may be provided for one or any subset of the extracted facts.

In some embodiments, automatically extracted clinical facts may also be automatically reviewed, and automatic alerts may be provided to the clinician or other user if opportunities are identified for the clinical documentation of the patient encounter to be improved. Such alerts may be visual alerts, audio alerts, or any other suitable type of alerts, as aspects of the present disclosure are not limited in this respect. In some embodiments, such alerts may be provided to the clinician or other user at a time subsequent to the completion of the patient encounter, and may provide the opportunity for the clinician or other user to provide additional information that was ascertained from the patient encounter but was not originally specified in the free-form narration. In other embodiments, such alerts may be provided to the clinician while the patient encounter is still in progress, and may provide the opportunity for the clinician to initiate further interaction with the patient to ascertain additional information to include in the clinical documentation.

In some embodiments, a fact review system may be programmed with a set of deterministic rules to trigger alerts. For example, a set of deterministic rules may specify that certain extracted facts, certain combinations of extracted facts, certain combinations of extracted facts and terms in the free-form narration, and/or certain combinations of facts extracted from the current patient encounter and facts from the patient's previous history automatically trigger alerts to the user. In other embodiments, the fact review system may be programmed to undertake a probabilistic analysis or apply a statistical model to determine whether information specified in the free-form narration will trigger alerts to the user. It should be appreciated, however, that a fact review system in accordance with embodiments described herein is not limited to any particular programming technique, as any suitable such technique may be used. In addition, it should be appreciated that automatic alerts may also be provided in embodiments that do not involve automatic extraction of clinical facts from a free-form narration. For example, such alerts may also be triggered by clinical facts received as discrete structured data items, such as direct input to an electronic medical record such as an EHR. It should thus be appreciated that alerts may be provided based on analysis of clinical facts collected in any suitable way, as aspects of the present disclosure are not limited in this respect.

In some embodiments, an alert may be provided when a set of one or more clinical facts is collected from a patient encounter, and it is determined that there is an opportunity to increase the specificity of the set of facts. In some embodiments, it may be determined that an additional fact may possibly be ascertained from the patient encounter, and that the additional fact would add specificity to the set of clinical facts already collected from the patient encounter. In one example, such an additional fact may be a more specific version of one of the original facts, and the specificity of the set of facts may be increased by replacing the original fact with its more specific version, provided that it can truly be ascertained from the patient encounter. For instance, the original fact may describe a condition, and the more specific version may describe the same condition as "acute" or "chronic". In another example, two or more of the original facts, when appearing in combination, may imply an additional fact, and documenting the additional fact may increase the specificity of the record of the patient encounter. In some embodiments, an alert may query the user as to whether an additional fact should actually be ascertained from the patient encounter, and may allow the user to increase the specificity of the facts by documenting the additional fact.

In some embodiments, an alert may be provided when a set of one or more clinical facts is collected from a patient encounter, and it is determined that a diagnosis that was not specified in the set of facts may possibly be ascertained from the patient encounter. In one example, such an unspecified diagnosis may be a known comorbidity of a diagnosis that was included in the set of facts. In another example, the unspecified diagnosis may be a known complication of a procedure or diagnosis included in the set of facts. In yet another example, the unspecified diagnosis may be an identification of the fact that a diagnosis included in the set of facts is actually a complication of a procedure or other diagnosis included in the set of facts, or of a procedure or other diagnosis included in facts from the patient's history prior to the current encounter. Similarly, the unspecified diagnosis may be an identification of the fact that a diagnosis included in facts from the patient's previous history is a complication of a diagnosis ascertained during the current patient encounter. In some embodiments, when the possibility or likelihood of such an unspecified diagnosis is determined from the original set of facts collected from the patient encounter, an alert may query the user (e.g., the clinician or another user) as to whether the unspecified diagnosis should be ascertained from the patient encounter.

In some embodiments, an alert may be provided when a set of one or more clinical facts is collected from a patient encounter, and it is determined that two or more of the facts in the set conflict with each other in some way, or it is determined that one or more of the facts in the set conflict with one or more facts in the patient's history. In some embodiments, a fact review system may be programmed to automatically generate such alerts based on a known set of combinations of facts that have undesirable interactions. For example, an alert may be generated when the set of facts indicate that the patient has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in a record of the patient's history with the institution. Thus, in some embodiments, the fact review system may access both facts collected from a current patient encounter and facts from the patient's historical records to determine whether alerts should be generated. In some embodiments, an alert to a conflict may be triggered by a combination of facts, at least one of which does not correspond to a medication. For example, alerts may be provided for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, an alert may be provided when a set of one or more clinical facts is collected from a patient encounter, and it is determined that there is an opportunity to add to the clinical documentation of the patient encounter for quality review purposes. In some embodiments, a fact review system may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as that of the Physician Quality Reporting Initiative (PQRI) or that of the Joint Commission on Accreditation of Healthcare Organizations (JCAHO). Any suitable quality of care standard may be used, as aspects of the present disclosure are not limited to any particular quality of care standard. In some embodiments, when a collected fact or combination of facts is associated with a certain recommended action on the part of the clinician according to the quality of care standard, an alert may be provided to query the user as to whether the recommended action was performed.

In some embodiments, a mechanism may be provided to adaptively filter the automatic alerts generated by the fact review system, by learning from the clinician's or other user's interaction with the system over time. For example, if it is determined that a particular user consistently ignores a particular type of alert, the system may stop issuing similar alerts when they are triggered by future facts. In some embodiments, the adaptive learning may be specific to each individual user and may help to prevent alert fatigue, which may involve frustration at repeatedly being bothered by an alert that the user does not find relevant. In some embodiments, the adaptive learning may involve the collection of data regarding patterns of facts that tend to be present when the user ignores alerts, and the system may filter out future alerts that match those patterns of facts. In some embodiments, adaptive alert filtering may be performed based on rules or statistical usage patterns on an institutional level, such that alerts not considered relevant for the specific healthcare institution in which the fact review system is operating are not provided.

In some embodiments, a human user other than the clinician may review the set of clinical facts collected from a patient encounter, and may manually (e.g., not automatically, but involving human action) cause one or more alerts to be issued to the clinician that were not issued automatically by the fact review system. Such a human user may manually cause alerts to be issued in any suitable way, as aspects of the present disclosure are not limited in this respect. In one example, the human user may provide instructional input to the fact review system to cause the fact review system to generate an alert specified by the human user. In other examples, the human user may use a different method and/or system, other than the fact review system, to issue an alert to the clinician. Such a different method in some embodiments need not be machine-based, as aspects of the present disclosure are not limited in this respect. In some embodiments, the human user may have access to the patient's past medical history within and/or external to the healthcare institution, for example in the form of an electronic medical record and/or past clinical documents relating to the patient's care at the institution and/or elsewhere. In some embodiments, the human user may make reference to this past medical history, in addition to the clinical facts from the current patient encounter, to determine whether to manually cause an alert to be issued to the clinician. In some embodiments, the human user may determine to issue an alert, similar to any of the various types of automatic alerts described above, if the facts and the patient's history indicate a situation in which the automatic fact review system should have generated an automatic alert, but it failed to accurately recognized the situation. In some embodiments, if the clinician chose to ignore an alert automatically generated by the fact review system, but ignoring such an alert was contrary to the policy of the institution, the human reviewer may determine to manually issue a follow-up alert to the clinician. Thus, in some embodiments, an automatic fact review system may coexist in an institutional setting with a manual review process involving a human user, and the manual review process may provide back-up and/or additional functionality to complement the automatic fact review processes.

In some embodiments, when medical facts are extracted from a free-form narration, a fact extraction component may encounter situations in which disambiguation is desired between multiple facts that could potentially be extracted from the same portion of the free-form narration. In one example, a term in the free-form narration might be linked to two different concepts in a formal ontology (described below) used by the fact extraction component, and it might not be likely that both of those concepts were intended to coexist in the free-form narration. In another example, the fact extraction component may apply a statistical model (examples of which are described below) to identify facts to be extracted from a certain portion of text, and the statistical model may come up with multiple alternative hypotheses for a single fact to be extracted. In some embodiments, the statistical model may be used to score the alternative hypotheses based on probability, confidence, or any other suitable measure of an estimated likelihood that each alternative accurately represents an intended semantic meaning of the portion of text from which it is to be extracted. In such situations, a fact review system in some embodiments may provide an interface to receive user input to disambiguate between multiple facts tentatively extracted by the fact extraction component. Such a user interface can be in any suitable form, as aspects of the present disclosure are not limited in this respect. In one non-limiting example, the fact review system may present to the user a certain number of the alternative hypotheses having high estimated likelihood scores. In some embodiments, each of the options provided may correspond to one of the multiple tentative facts, and the user may choose one of the options to specify which fact should actually be extracted from the free-form narration.

In some cases, when the user makes a selection of a fact presented through a structured choice provided by the fact review system, the set of facts extracted by the fact extraction component may be updated accordingly, but the original free-form narration from which the facts were extracted may remain unchanged. In some embodiments, in other cases, a textual representation of the clinician's free-form narration may automatically be updated (e.g., changed) to explicitly identify the user's selected fact as having been ascertained from the patient encounter. For example, if the free-form narration originally included a term linked to two different concepts in the fact extraction component's ontology, the fact review system could present the user a structured choice between a different term linked only to one of the concepts and a different term linked only to the other of the concepts. When the user selects one of the different terms in the structured choice presented, in some embodiments the text narrative may automatically be updated to replace the original term with the selected term. In another example, if application of a statistical fact extraction model resulted in multiple alternative hypotheses for a fact to be extracted from a certain portion of the free-form narration, the fact review system could present the user a choice between at least two of the alternative hypotheses (e.g., the N alternative hypotheses having the highest scores). In some cases in some embodiments, the text narrative may automatically be updated to better reflect the alternative hypothesis selected by the user. For example, if the original text narrative included the term "asthma," the fact extraction component might present alternative fact hypotheses of "chronic obstructive asthma" and "asthma unspecified." If the user then selects the "chronic obstructive asthma" hypothesis (representing a more specific asthma fact), the text narrative could then automatically be updated to replace the original "asthma" term with "chronic obstructive asthma." In some embodiments, such updating of the text narrative may be performed in response to any type of user selection of an option provided by the fact review system, corresponding to a medical fact that could possibly be ascertained from the patient encounter. Some examples include disambiguating options, options corresponding to additional facts for increased specificity and options corresponding to unspecified diagnoses, as discussed above. In some embodiments, rather than replacing text in the narrative, new text corresponding to the selected fact may be generated and simply added to the narrative in one or more appropriate locations. In some embodiments, the location(s) at which to insert text identifying the selected fact may be automatically determined by identifying one or more section headings in the text narrative, and by inserting the text in the section or sections most closely corresponding to the selected fact.

In some embodiments, a fact review system may allow a clinician or other user to directly add a clinical fact as a discrete structured data item, and to indicate a linkage to a portion of the clinician's free-form narration of the patient encounter from which the added fact should have been extracted. For example, the user may specify a clinical fact as a discrete structured data element, select a word or set of words (which need not be contiguous) in the free-form narration, and indicate that the specified fact is ascertained from that portion (e.g., that word or set of words) of the free-form narration. In some embodiments, when such a fact is added, the fact extraction component may be updated for that user (or for the clinician who provided the free-form narration), e.g., to link the selected word(s) from the free-form narration to one or more concepts in a formal ontology corresponding to the added fact, or to re-train a statistical fact extraction model to associate the selected word(s) with the added fact. In some embodiments, the free-form narration may further be re-processed by the updated fact extraction component to extract any further additional facts that may be determined based on the updated terminology. In one example, if the user selected a word in the patient history section of the free-form narration, and added a fact specifying that the patient has a history of a particular condition, the updated fact extraction component re-processing the free-form narration might identify the same word in the family history section, and extract an additional fact that the patient has a family history of the same condition. In some embodiments, such automatic re-processing may spare the clinician or other user the time and effort that otherwise would be required to define multiple facts corresponding to the same terminology in the free-form narration. In some embodiments, similar re-processing may be performed when the user edits or deletes a fact originally extracted automatically from the free-form narration, when the fact is linked to terminology that appears in multiple parts of the free-form narration.

In some embodiments, as discussed above, a fact review system may allow a user to add, delete and/or modify (collectively referred to as "change") a medical fact extracted from a free-form narration of a patient encounter provided by a clinician, resulting in a change to the set of extracted facts. For example, in some embodiments, a user may add a fact to the set of extracted facts, e.g., by specifying a portion of the free-form narration and specifying a particular fact that should be extracted from that portion of the narration. In some embodiments, a user may specify an added fact directly, e.g., by typing, speaking, or otherwise inputting the particular fact to be added, or by selecting the fact and/or components of the fact from menu options. Alternatively or additionally, as described above, in some embodiments the system may present the user with a choice between multiple alternative hypotheses for a fact to be extracted from a portion of the free-form narration, and the user may select one of the presented hypotheses to add that fact to the set of extracted facts. In another example, a user may modify a fact already automatically extracted from the free-form narration, e.g., by selecting the extracted fact and inputting a different fact with which it should be replaced, or by selecting a component of the extracted fact and inputting a change to that component, etc. In another example, a user may delete an extracted fact, e.g., by selecting the extracted fact and selecting a "delete" option, or otherwise indicating that that fact should not have been extracted from the corresponding portion of the free-form narration. It should be appreciated, however, that the foregoing are merely examples, and a user may be allowed to add, delete and/or modify one or more facts in a set of extracted medical facts in any suitable way, as aspects of the present disclosure are not limited in this respect.

When a user inputs a change (e.g., an addition, deletion, or modification) to a set of one or more facts already automatically extracted from a free-form narration, such a change is referred to herein as a "correction" to the set of extracted facts. In some embodiments, a user may input a correction to an extracted set of medical facts in any suitable way, and the fact review system may then apply the user's correction throughout the free-form narration. In such a way, in some embodiments, a user may be able to correct the fact extraction component's treatment of one portion of the narrative text, and similar corrections may then be applied automatically to other portions of the text, without the user having to directly specify the same type of correction for every similar portion of text in the document. For a non-limiting example, consider the illustrative narrative text below:
CHIEF COMPLAINT: Epileptic myoclonic twitches of the upper extremity.
PAST MEDICAL HISTORY: History of developmental delay and myoclonic seizure involving the upper extremities.
ASSESSMENT: Myoclonic jerks involving the upper extremities.

Assume that an automatic fact extraction component failed to extract the clinician's intended meaning (the intended medical fact) from the text portion "Epileptic myoclonic twitches of the upper extremity." The text portions "myoclonic seizure involving the upper extremities" and "Myoclonic jerks involving the upper extremities" communicate similar semantic meanings, so the automatic fact extraction component is unlikely to successfully extract the intended medical fact from these text portions either. In some embodiments, a user could correct the fact extraction by selecting the text portion "Epileptic myoclonic twitches," and adding a corresponding medical fact "myoclonic epileptic seizure," which corresponds to ICD-9 code 345.1. In some embodiments, upon analyzing the user's correction to the fact extraction from the first portion of the text, the fact review system may learn from the association and may automatically apply similar corrections to the rest of the narrative text. For example, the fact review system may identify the other text portions "myoclonic seizure" and "myoclonic jerks" as being similar to the first text portion "Epileptic myoclonic seizures," and may automatically extract the fact "myoclonic epileptic seizure," corresponding to ICD-9 code 345.1, from the other two text portions as well. In this example, in some embodiments, the system may extract similar facts (e.g., facts that are not necessarily identical to the fact added by the user) from the other portions of the text, since the other text portions may have similar, but not necessarily identical, intended semantic meanings as the first text portion. For example, in the above narrative, both text portions "Epileptic myoclonic twitches" and "myoclonic seizure" indicate a medical problem with a normalized form of "myoclonic epileptic seizure," but the second portion occurs in the "PAST MEDICAL HISTORY" section, while the first portion occurs in the "CHIEF COMPLAINT" section. Thus, in some embodiments, the system may automatically extract a similar medical fact from the second portion, but the fact extracted from the second portion may indicate that the problem is a past history problem rather than a current problem.

Thus, in some embodiments, a user may identify a fact that should be associated with a first portion of the narrative text, and the system may then automatically extract one or more similar facts from one or more other portions of the narrative text. The user may identify the fact that should be associated with the first text portion in any suitable way. For example, as discussed above, in some cases the user may select a portion of the narrative text, and may directly specify a fact that should be extracted from that portion of the text. In other cases, the fact extraction component may present to the user multiple options corresponding to alternative hypotheses for a fact to be extracted from the portion of the narrative text, and the user may identify the fact that should be associated with that text portion by selecting one of the alternative hypotheses presented. In still other cases, a user may select a fact that was already extracted from a portion of the narrative text, and may specify a modification that should be made to the extracted fact, thus identifying the correct fact that should be associated with the text portion. It should be appreciated, however, that the foregoing are merely examples, and a user may identify a fact that should be associated with a portion of the narrative text in any suitable way, as aspects of the present disclosure are not limited in this respect.

In still other examples, a user may delete a fact that was extracted from a first portion of the narrative text, and the system may then automatically delete one or more other instances of the same extracted fact (or of similar extracted facts) from one or more other portions of the narrative text. It should further be appreciated, however, that adding, deleting, and modifying facts as described above are only examples, and the user may be permitted to correct a set of extracted medical facts in any suitable way, as aspects of the present disclosure are not limited in this respect. In some embodiments, any suitable type of correction made by a user to one or more facts extracted from a first portion of a narrative text may then automatically be applied to one or more other portions of the narrative text. Furthermore, in some embodiments, any suitable type of correction made by a user to a set of facts extracted from a first narrative text may alternatively or additionally be automatically applied to other narrative texts processed by the fact extraction component in the future. In some embodiments, one or more fact extraction models used by the fact extraction component may be re-trained such that the correction applied to the first text may be reflected in the manner of processing later texts. Illustrative techniques for applying a user correction throughout the text in which it occurs, as well as illustrative techniques for reflecting such a correction in the processing of other texts, are described below.

In some instances, one or more such changes made to the set of facts corresponding to the current patient encounter may create one or more inconsistencies between the set of facts and the semantic content of the original free-form narration. For example, a clinician may originally specify a particular diagnosis in a free-form narration, and a fact extraction component may extract a clinical fact corresponding to that diagnosis. If the clinician later changes his mind and would like to replace the original diagnosis with a different diagnosis, he may have the option in some embodiments of simply editing the extracted fact directly, rather than editing the data representation of the free-form narration itself. Such a situation may create an inconsistency between the free-form narration and the corresponding set of clinical facts, as the facts may now specify the new diagnosis, and the free-form narration may still specify the original diagnosis. In such situations, the fact review system in some embodiments may alert the clinician or other user to the inconsistency, and/or may provide any of several options to the user to address the inconsistency. One option may be to ignore the inconsistency and allow it to persist in the clinical documentation. Another option may be to allow the user to edit the data representation of the free-form narration to be consistent with the current set of clinical facts. Another option may be to allow the system to automatically update the data representation of the free-form narration by adding, deleting or replacing one or more portions of the free-form narration. Yet another option may be simply to append a note to the free-form narration, indicating and optionally explaining the inconsistency.

In some embodiments, as discussed above, a medical fact review system may provide various tools for a clinician to review and/or edit facts corresponding to a current patient encounter, receive alerts generated based on those facts, review and/or edit a free-form narration of the patient encounter provided by the clinician, and/or review the linkages maintained between medical facts extracted by a fact extraction component and the portions of the free-form narration from which the medical facts were extracted. Such tools may be provided in any suitable form, including visual forms, audio forms, combined forms or any other form providing the functionality described herein, as aspects of the present disclosure are not limited in this respect. When the tools are provided in visual form, their functionality may be accessed through a graphical user interface (GUI). In some embodiments, the GUI may be organized in a way to allow the human user(s) to efficiently process the information displayed. For example, in some embodiments, text narratives, facts and alerts may be displayed in consistent locations within the user interface and organized by type and/or priority. Different colors, textual styles and/or graphical styles may be utilized to direct the user's attention to high-priority alerts, and/or to make linkages between related items in the display easily recognizable. In some embodiments, the organization and/or composition of such a visual display may be determined in accordance with principles used in the development of heads-up displays (HUDs).

In some embodiments, a fact review system operating on a set of clinical facts ascertained from a patient encounter may provide tools for promoting efficiency in the workflow of the clinician and/or other personnel beyond the conclusion of the patient encounter. For example, in some embodiments, the fact review system may interface with one or more Computerized Physician Order Entry (CPOE) systems to automatically place orders for prescriptions, laboratory tests, radiology screenings, surgical or other medical procedures and/or other planned treatment action items, based on such items (e.g., medication names, dosages, procedure names, dates, etc.) being specified in the set of facts corresponding to the current patient encounter. In some embodiments, such items may be identified based on their being extracted from a "plan" section of a free-form narration. In some embodiments, the fact review system may interface with one or more scheduling systems to schedule appointments for medical procedures and/or future office visits within or external to the institution. In some embodiments, the fact review system may format one or more facts into a standard or proprietary messaging format to facilitate interfacing with any of such systems. In some embodiments, billing reports, patient discharge instructions and/or other documents may be automatically generated or initially populated based on the set of clinical facts. In some embodiments with any of the above-described functionality, the fact review system may provide an alert to the user and/or may prompt for user or clinician approval prior to taking any of the above actions.

In some embodiments, a fact review system may provide tools for evidence-based clinical decision support based on the set of clinical facts collected for the current patient encounter. In some embodiments, the fact review system may have access to one or more data sets of past patient reports and/or one or more archives of medical literature documents that may provide information regarding various conditions, treatment outcomes and the like that are relevant to the current patient encounter. In some embodiments, the available documents may have been processed by the fact extraction component and indexed using the same system of terminology used to extract clinical facts from free-form clinical narrations. As such, in some embodiments, the facts corresponding to the current patient encounter may be efficiently matched to relevant available documents, and those documents or a subset thereof may be retrieved for display or otherwise provided to the clinician to aid in his determination of a treatment plan for the current patient. In some embodiments, a statistical model may be trained on the data set of past patient outcomes and/or on data in the medical literature, such that the system may go beyond mere presentation of references to actually predict best courses of treatment by applying the statistical model to the collection of facts corresponding to the current patient encounter and/or to the patient's medical history. In some embodiments, treatment recommendations may be provided to the clinician along with links to references in the literature or other available data supporting the recommendations. In some embodiments, clinical language understanding (CLU) indexing of large quantities of patient records and/or literature documents may also be used to facilitate clinical research studies, as available natural language documents may be efficiently mapped to an ad hoc query corresponding to a research question. From the resulting corpus of conceptually relevant documents, treatment outcomes and/or other required information or facts may be extracted using CLU technology to aid in synthesizing an answer to the research question.

While a number of inventive features for clinical documentation processes are described above, it should be appreciated that embodiments of the present disclosure may include any one of these features, any combination of two or more features, or all of the features, as aspects of the present disclosure are not limited to any particular number or combination of the above-described features. The aspects of the present disclosure described herein can be implemented in any of numerous ways, and are not limited to any particular implementation techniques. Described below are examples of specific implementation techniques; however, it should be appreciate that these examples are provided merely for purposes of illustration, and that other implementations are possible.

Figure 8:
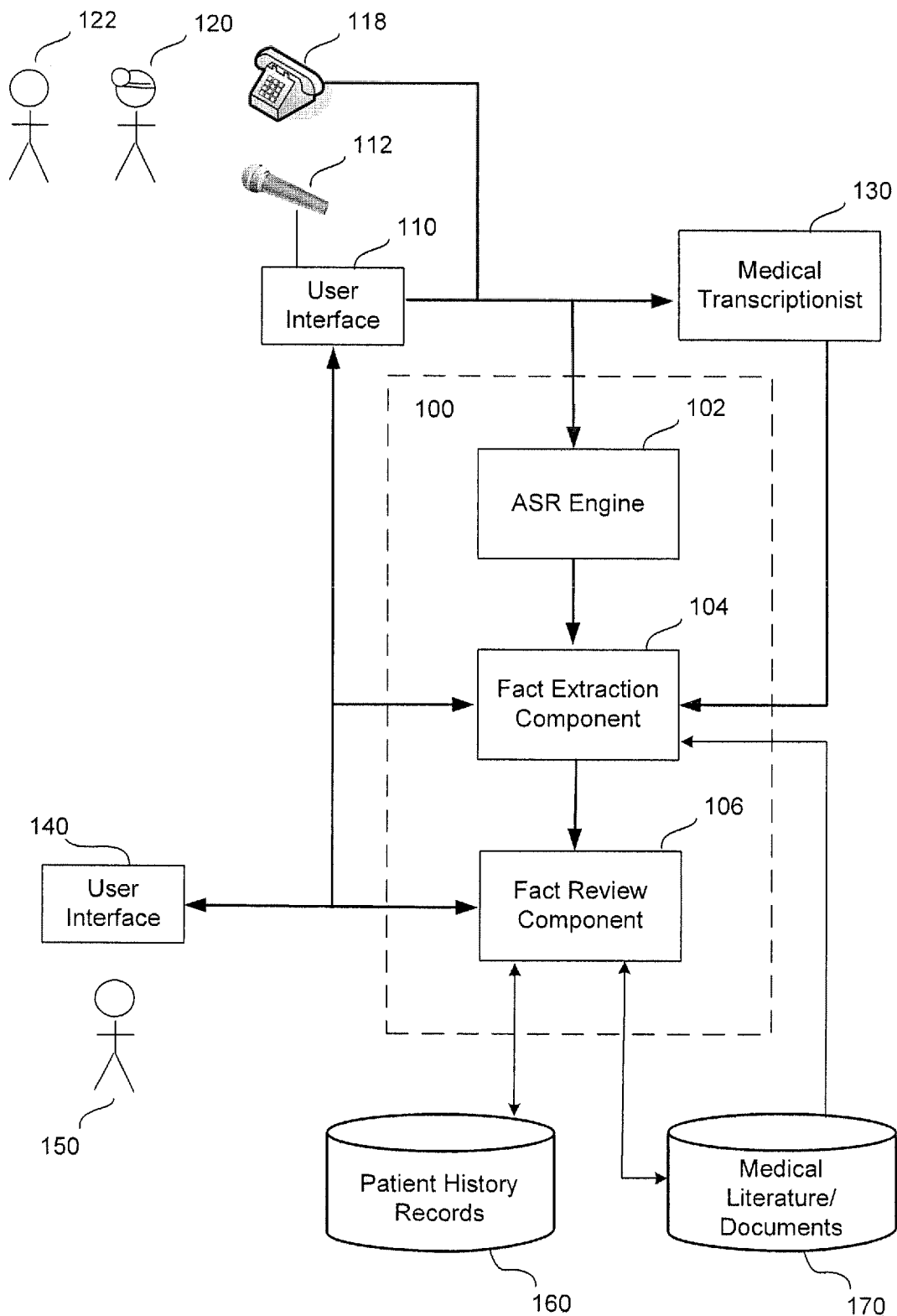
FIG. 8 shows an illustrative operating environment for a medical fact extraction system, in accordance with some embodiments.

One illustrative application for the techniques described herein is for use in a system for enhancing medical documentation processes. An illustrative operating environment for such a system is illustrated in FIG. 8. The illustrative operating environment includes a medical documentation system 100, which may be implemented in any suitable form, as aspects of the present disclosure are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, illustrative system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 8 is not limited to any particular software and/or hardware implementation and/or configuration.

As illustrated in FIG. 8, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, illustrative functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present disclosure are not limited in this respect.

Another way to provide a free-form narration of the patient encounter may be to verbally speak a dictation of the patient encounter. Such a spoken dictation may be provided in any suitable way, as aspects of the present disclosure are not limited in this respect. As illustrated in FIG. 8, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Illustrative functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present disclosure are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as aspects of the present disclosure are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the present disclosure are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the present disclosure are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as aspects of the present disclosure are not limited in this respect. One illustrative technique suitable for performing re-formatting of a text narrative is described in U.S. patent application Ser. No. 11/322,971, filed on Dec. 30, 2005, entitled "Translating Literal Speech to Formatted Text", which is incorporated herein by reference in its entirety. Another illustrative technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models in some embodiments may be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present disclosure are not limited in this respect. Illustrative techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present disclosure are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present disclosure are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the present disclosure are not limited in this respect. In addition, a knowledge representation model such as an ontology used by fact extraction component 104 may be constructed in any suitable way, as aspects of the present disclosure are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that aspects of the present disclosure are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input.

Illustrative implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the present disclosure are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the present disclosure are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the present disclosure are not limited in this respect.

A section normalization module may use any suitable technique to associate portions of text with normalized document sections, as aspects of the present disclosure are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the present disclosure are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one illustrative implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely illustrative, as any suitable features may be used. Aspects of the present disclosure are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the present disclosure are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the present disclosure are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the present disclosure are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the present disclosure are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the present disclosure are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that is chronic and not, e.g., acute. Another illustrative type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the present disclosure are not limited to any particular attributes for any particular fact types. Also, other types of fact relations are possible, including family relative relations, causes-problem relations, improves-problem relations, and many others. Aspects of the present disclosure are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the present disclosure are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely illustrative, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Illustrative techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the present disclosure are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the present disclosure are not limited in this respect. Illustrative standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Illustrative techniques that may be used in some embodiments are described in Salton, Wong, & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments, as aspects of the present disclosure are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the present disclosure are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One illustrative implementation of such a user interface is graphical user interface (GUI) 200, illustrated in FIG. 9. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the present disclosure are not limited in this respect. While the illustrative embodiments illustrated in FIG. 8 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the present disclosure are not limited to any particular distribution of local and/or remote processing capabilities.

Figure 9:
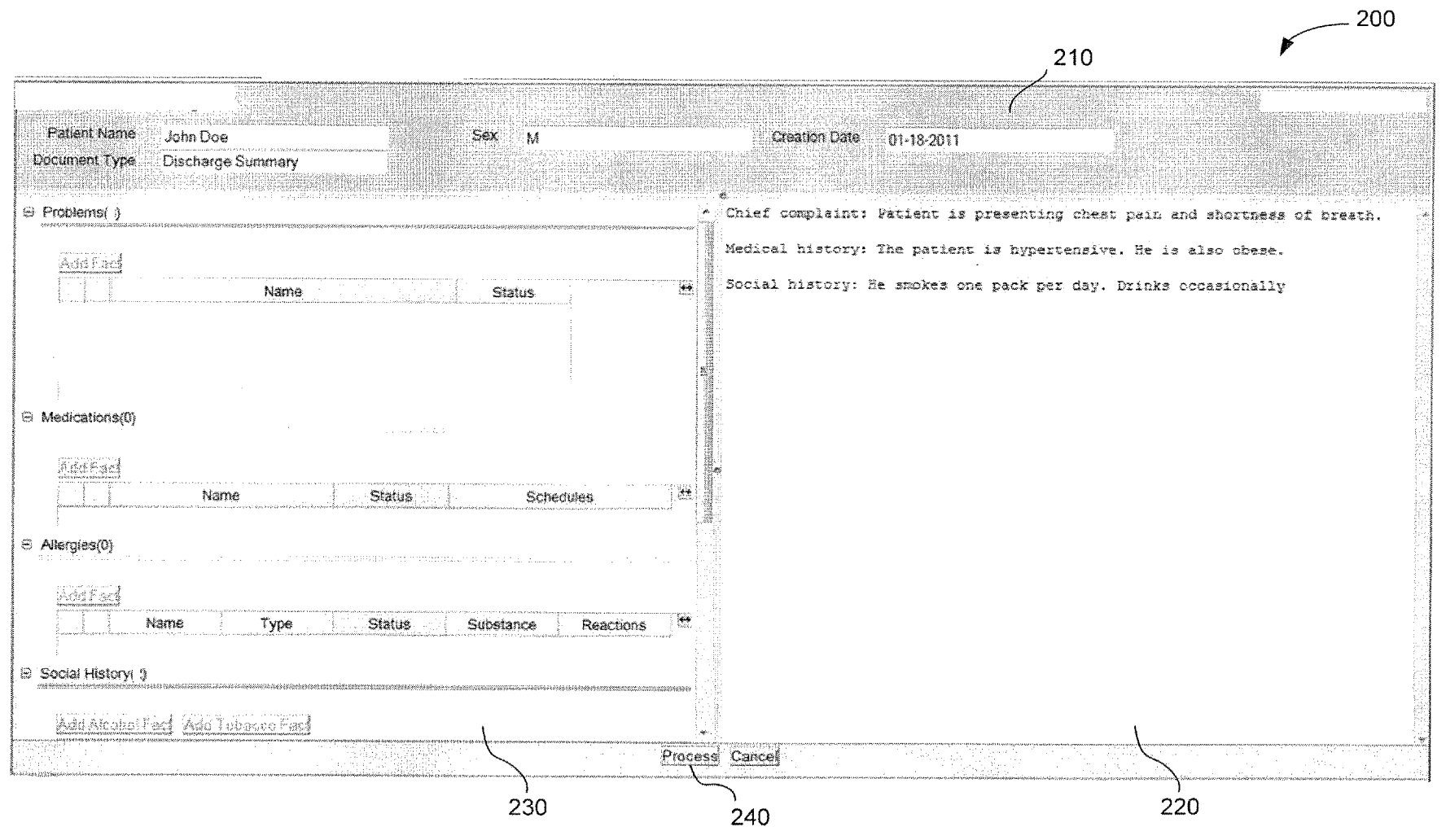

As depicted in FIG. 9, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the present disclosure are not limited in this respect.

GUI 200 as depicted in FIG. 9 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Illustrative GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 10A:
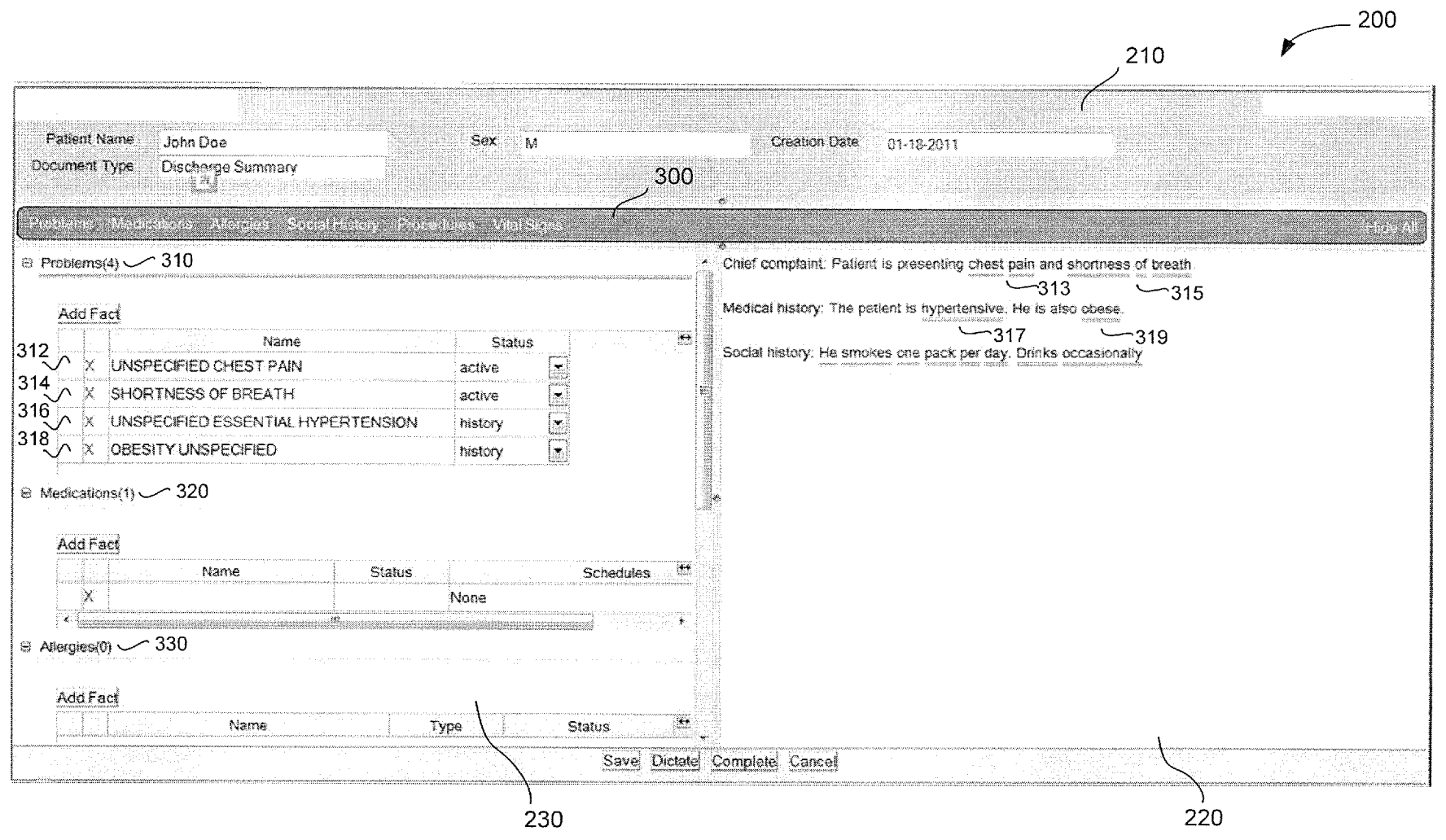
Figure 10B:
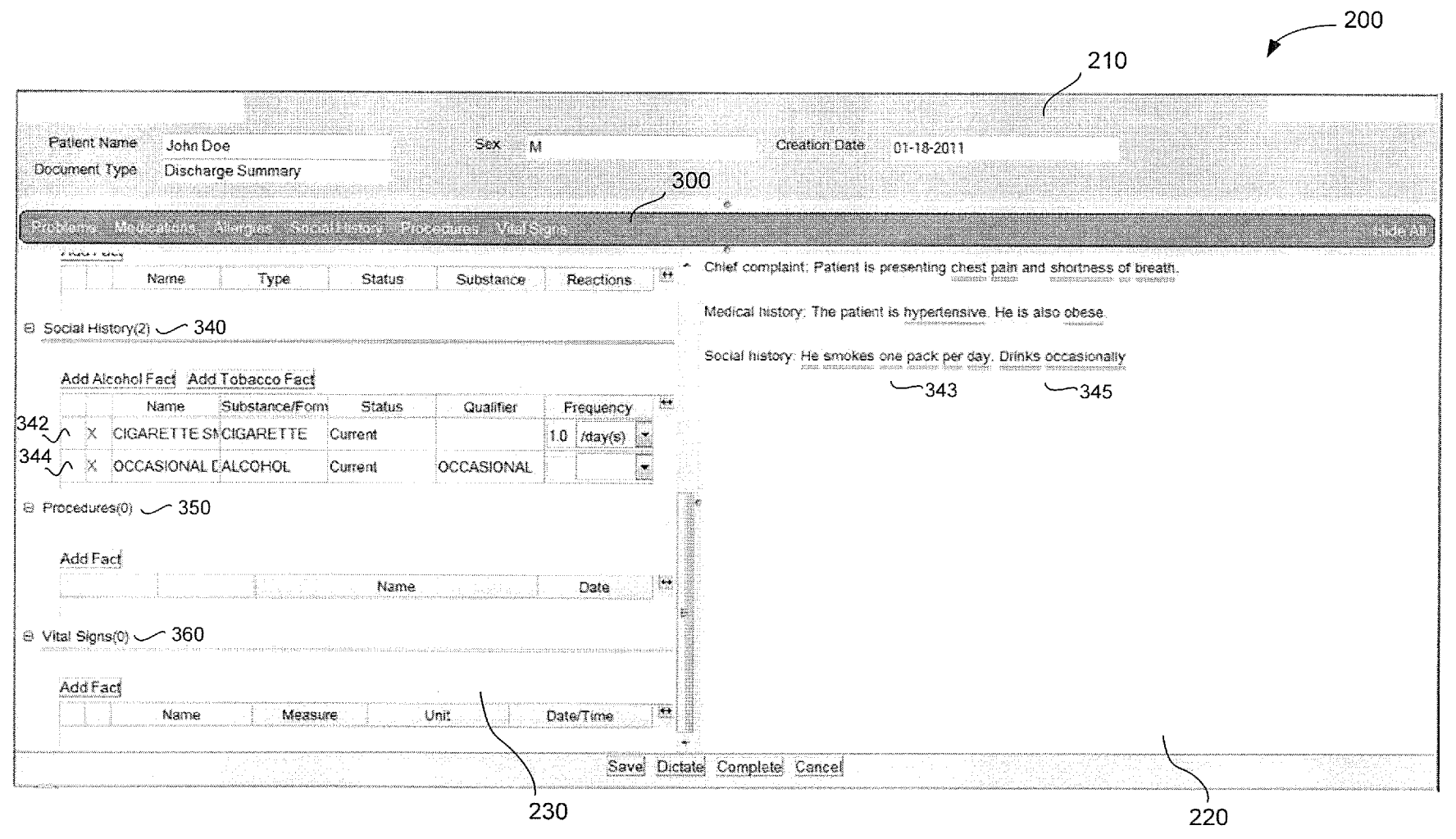

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 10A and 10B. FIG. 10A is a screenshot with fact panel 230 scrolled to the top of a display listing medical facts extracted from the example text narrative, and FIG. 10B is a screenshot with fact panel 230 scrolled to the bottom of the display listing the extracted medical facts. In some embodiments, as depicted in FIGS. 10A and 10B, medical facts corresponding to a patient encounter may be displayed in fact panel 230, and organized into a number of separate categories of types of facts. An illustrative set of medical fact categories includes categories for problems, medications, allergies, social history, procedures and vital signs. However, it should be appreciated that any suitable fact categories may be used, as aspects of the present disclosure are not limited in this respect. In addition, organization of facts into categories is not required, and displays without such organization are possible. As depicted in FIGS. 10A and 10B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 10A and 10B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 10A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 10A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An illustrative list of fact categories and their component fields is given below. However, it should be appreciated that this list is provided by way of example only, as aspects of the present disclosure are not limited to any particular organizational system for facts, fact categories and/or fact components.

Illustrative List of Fact Categories and Component Fields

Category: Problems. Fields: Name, SNOMED status, ICD code.

Category: Medications. Fields: Name, Status, Dose form, Frequency, Measures, RxNorm code, Administration condition, Application duration, Dose route.

Category: Allergies. Fields: Allergen name, Type, Status, SNOMED code, Allergic reaction, Allergen RxNorm.

Category: Social history—Tobacco use. Fields: Name, Substance, Form, Status, Qualifier, Frequency, Duration, Quantity, Unit type, Duration measure, Occurrence, SNOMED code, Norm value, Value.

Category: Social history—Alcohol use. Fields: Name, Substance, Form, Status, Qualifier, Frequency, Duration, Quantity, Quantifier, Unit type, Duration measure, Occurrence, SNOMED code, Norm value, Value.

Category: Procedures. Fields: Name, Date, SNOMED code.

Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 10A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the present disclosure are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the present disclosure are not limited in this respect.

Fact panel 230 scrolled to the bottom of the display as depicted in FIG. 10B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 11:
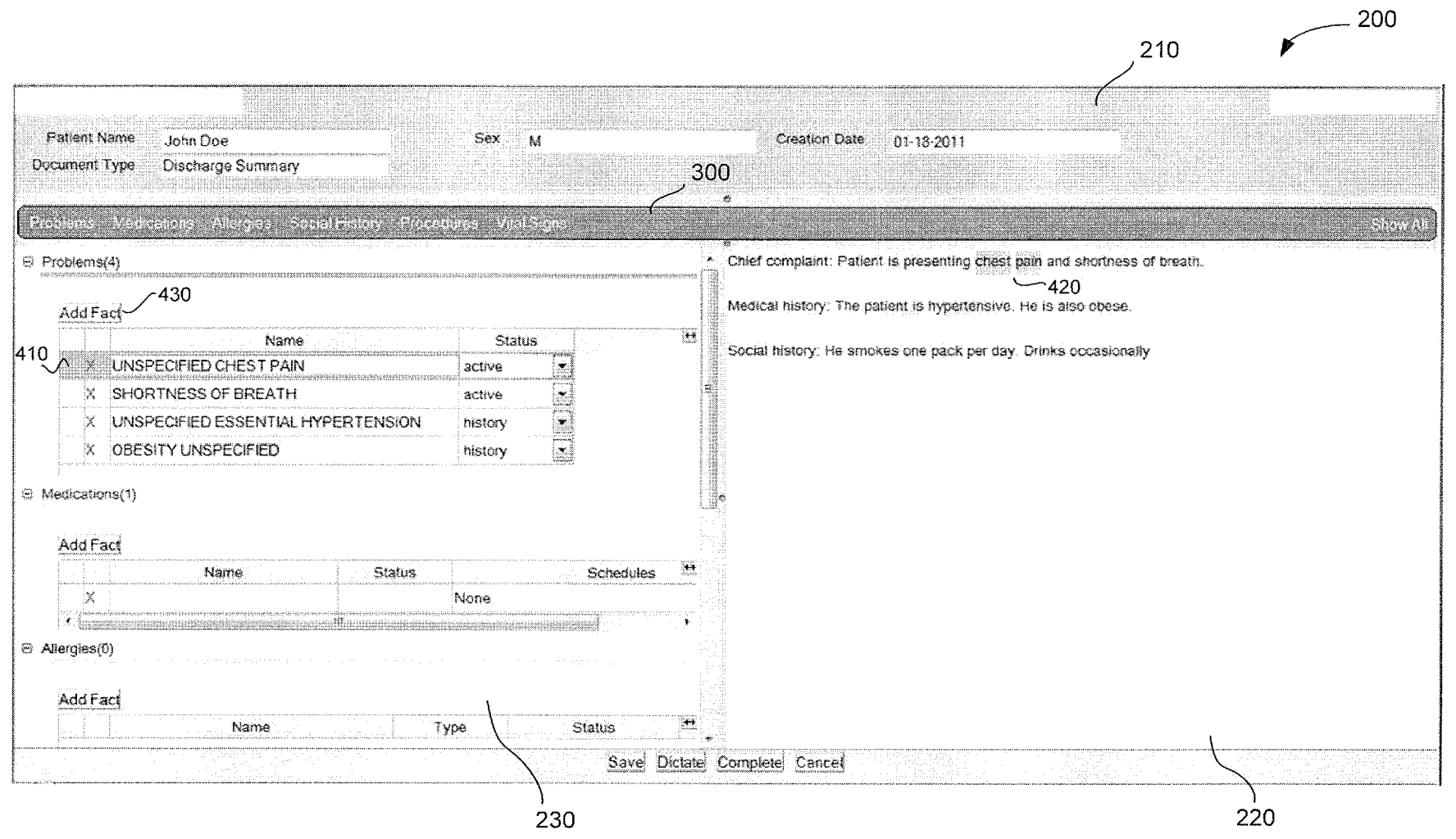

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 11. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the present disclosure are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the present disclosure are not limited in this respect. In addition, aspects of the present disclosure are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the present disclosure are not limited in this respect.

In some embodiments, GUI 200 may be configured to provide any of various ways for the user to make one or more changes to the set of medical facts extracted from the text narrative by fact extraction component 104 and displayed in fact panel 230. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 10A and FIG. 11, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

In some embodiments, GUI 200 may be configured to provide any of various ways for one or more facts to be added as discrete structured data items. As depicted in FIG. 11, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category. It should be appreciated that this is merely one example, as aspects of the present disclosure are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the present disclosure are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present disclosure are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

In some embodiments, one or more medical facts, either automatically extracted from a text narrative by fact extraction component 104 or directly entered by a user as discrete structured data items, may be input to fact review component 106 for automatic review. In some embodiments, fact review component 106 may be programmed to identify opportunities for the medical documentation of the patient encounter to be improved, and if any such opportunities are identified, to provide an alert to the user (e.g., clinician 120 or other user 150). Some examples of alerts that may be provided are described above. As discussed, any suitable form of alert, including visual and/or audio alerts, may be used, as aspects of the present disclosure are not limited in this respect. In some embodiments, the review of collected medical facts to determine opportunities for improved medical documentation, and the resulting alerting and/or querying of the user, may be performed entirely automatically by fact review component 106 or any other suitable component. As used herein, performing a process "automatically" refers to having no required human participation between the input to the process and its corresponding output, with all intervening acts performed by machine.

As discussed above, one type of alert that may be provided to a user by fact review component 106 is an alert of a potential opportunity to increase the specificity of the set of facts ascertained from the patient encounter. This can be done in any suitable way. In some embodiments, fact review component may be programmed with a set of deterministic rules to decide when such a potential opportunity exists. For example, in some embodiments, if a clinical term corresponding to one of the facts is linked to a concept in the formal ontology used by fact extraction component 104, and that concept is a parent to one or more more specific child concepts in the ontology, then fact review component 106 may generate an alert to query the user as to whether one of the more specific child concepts can actually be ascertained from the patient encounter. If the user answers in the affirmative, in some embodiments fact review component 106 may cause the more general fact to be replaced by a more specific version indicated by the user. Similarly, if one or more concepts in the formal ontology are linked to clinical terms appearing in the set of facts, and if those concepts have relationships in the ontology to a fact that could add specificity to the set of facts, and alert and/or query may be generated. As an example, if one or more conditions documented in the set of facts are known through ontological relationships to be symptoms of a specific diagnosis, in some embodiments fact review component 106 may query clinician 120 or other user 150 as to whether the specific diagnosis may be ascertained from the patient encounter and added to the facts. In some embodiments, as an alternative or in addition to the set of deterministic rules, a statistical model may be used to identify situations in which a potential opportunity to increase the specificity of the set of facts exists.

In another example, one or more of the facts in the set collected (either by fact extraction from a text narrative or by direct entry as one or more discrete structured data items) from the patent encounter may correspond to one or more standard codes used for billing, ordering, evaluating quality of care, or the like. Such standard codes may be specific to the healthcare institution or may be a standard shared by multiple institutions. Examples of such standard coding systems include, but are not limited to, ICD codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes. Some such standard coding systems are hierarchical, in that certain codes within the system are more specific versions of other codes within the system. For example, in the ICD-10 coding system, code I20 represents "angina pectoris" (chest pain due to lack of blood and oxygen to the heart muscle). More specific versions of ICD-10 code I20 include I20.0 ("unstable angina"), I20.1 ("angina pectoris with documented spasm"), I20.8 ("other forms of angina pectoris") and I20.9 ("angina pectoris, unspecified"). In some embodiments, if one of the set of facts collected from the patient encounter includes a general-level code such as ICD-10 I20, fact review component 106 may be programmed to automatically query the user as to whether one of the corresponding specific-level codes could be ascertained from the patient encounter instead. In some embodiments, fact review component 106 may present the user with a structured choice among the available specific-level codes, and may allow the user to choose among the available options.

In another example, fact review component 106 may be programmed to alert the user when a specific fact may be implied by the combination of two or more facts appearing together in the set of facts collected from the patient encounter. One example is a set of facts that included a diagnosis of pneumonia as well as a test result indicating that pseudomonas was found in a sputum culture. Based on a deterministic rule, or a statistical model result, indicating that these two facts in combination may imply a more specific form of pneumonia due to the presence of an organism, fact review component 106 may query the user as to whether the more specific diagnosis can be ascertained from the patient encounter.

In some embodiments, an alert that would otherwise be generated from the current patient encounter may be suppressed if there is information in the patient's medical history that already provides the additional specificity. To this end, in some embodiments fact review component 106 may have access to a data set of patient history records 160 for patient 122, and may query patient history records 160 for such information prior to generating an alert to the user. For example, if the set of facts from the current patient encounter specifies a condition but does not specify whether it is "acute" or "chronic", but a previous record in patient history records 160 already specifies that the condition is "chronic", then fact review component 106 in some embodiments may automatically edit the set of facts for the current patient encounter to specify that the condition is "chronic", without bothering the user with an alert. However, in some embodiments, even if fact review component 106 can obtain such specificity enhancing information automatically, a message may still be generated to inform the user that the information is being automatically added, and to allow the user to reject the change if desired, or to ask the user to approve of the change being made.

In some embodiments, if it is a user 150, and not clinician 122, who responds to an alert to increase the specificity of a set of clinical facts for a patient encounter, clinician 120 may be prompted to approve any additional information provided by the other user 150 prior to finally approving the set of facts for the patient encounter. For example, in some embodiments user 150 may be a coding specialist who is assigned the task of reviewing and editing the set of clinical facts (which may include billing codes) into a version fit to be incorporated into an electronic medical record, patient reports, order forms, or other document types. In such a "back-end" arrangement, the set of clinical facts settled upon by coding specialist 150 may then in some embodiments be transmitted to clinician 120 to give final approval to the set of facts. In some other embodiments, coding specialist 150 may not be required. For example, in a "front-end" arrangement, clinician 120 may review and possibly edit the set of clinical facts himself, and finally approve the set of facts when he is satisfied. This may occur during the patient encounter in some embodiments, or at some time thereafter (e.g., before clinician 120 finally approves or signs off on the report) in other embodiments. In either type of arrangement, in some embodiments, processing by fact review component 106 or any other component to provide alerts, decision support, workflow tools or the like in relation to the set of facts may be performed prior to the clinician's final approval of the set of facts.

In some embodiments, similar processing may be performed by fact review component 106 to alert the user when it is determined that an unspecified diagnosis may possibly be ascertained from the patient encounter. As discussed above, examples of such unspecified diagnoses include comorbidities of one or more already specified diagnoses, and identification of one or more already specified diagnoses as complications of one or more other specified diagnoses and/or procedures. For example, if the set of facts collected for the patient encounter specified a diagnosis of pneumonia, and the patient's oxygen saturation is also low, it may be determined that respiratory failure, a comorbidity of pneumonia, may possibly be ascertained from the patient encounter. In such a case, fact review component 106 may generate an alert to the user. In some embodiments, such determinations may be made based on knowledge of best practices, with deterministic rules providing reminders of diagnoses that should be investigated, for best quality of care, when other related conditions are present. In other embodiments, such determinations may be made statistically, by inputting the collected set of facts and/or facts from the patient's medical history to a statistical model trained on past clinical reports and/or medical literature. In this way, patterns of diagnoses that tend to be related may be identified statistically, and alerts may be generated based on the likelihood that relationships observed in the past will surface in the current patient encounter. To this end, in some embodiments, fact review component 106 may have access to a data set of medical literature/documents 170 (such as past clinical reports from the healthcare institution and/or from other sources) from which statistical models may be built and updated.

In some embodiments, as discussed above, fact review component 106 may be programmed to generate an alert when it determines that two or more of the facts in the set collected from the patient encounter conflict with each other in some way, or when it determines that one or more of the facts in the set conflict with one or more facts in patient history records 160. In some embodiments, fact review component 106 may be programmed to automatically generate such alerts based on a known set of combinations of facts that have undesirable interactions. For example, an alert may be generated when the set of facts indicate that patient 122 has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in patient history records 160. In some embodiments the known set of undesirable interactions may be represented in a data set locally accessible to fact review component 106, while in other embodiments, fact review component 106 may query one or more external data sets (such as those maintained by pharmacies) to determine whether given facts for patient 122 demonstrate any contraindications. In some embodiments, fact review component 106 or another suitable processing component may both maintain an internal data set and also query external data sets, for instance for periodic updates to the internal data set.

In some embodiments, an alert to a conflict may be triggered by a combination of facts, at least one of which does not correspond to a medication. For example, fact review component 106 may generate alerts for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, as discussed above, fact review component 106 may generate an alert when it determines that there is an opportunity to add to the clinical documentation of the patient encounter for quality review purposes.

In some embodiments, fact review component 106 may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as the PQRI standard or the JCAHO standard. Any suitable quality of care standard may be used, as aspects of the present disclosure are not limited to any particular quality of care standard. In some embodiments, when a collected fact or combination of facts is associated with a certain recommended action on the part of the clinician according to the quality of care standard, an alert may be provided to query the user as to whether the recommended action was performed. For example, if the set of facts specify that patient 122 is a smoker, in some embodiments fact review component 106 may generate an alert to remind clinician 120 to counsel patient 122 about quitting smoking, and to document the counseling in the patient record. In another example, if the set of facts specify that patient 122 presented with a heart attack, in some embodiments fact review component 106 may prompt clinician 120 to document how quickly aspirin was prescribed and/or administered, such that proof of compliance with the applicable quality of care standards may be documented. In some embodiments, fact review component 106 may be used to generate PQRI score reports, or the like, to send to insurance companies as compliance evidence to support reimbursement.

In some embodiments, as discussed above, fact review component 106 or another suitable component may generate an alert to the user when it determines that disambiguation is desired between multiple facts that could potentially be extracted from the same portion of the text narrative. For example, a term in the free-form narration might be linked to two different concepts in the formal ontology used by fact extraction component 104, and it might not be likely that both of those concepts were intended to coexist in the free-form narration. For example, if the text narrative contains the word "cold", it may be difficult in some cases for fact extraction component 104 to determine whether clinician 120 intended that word to mean that patient 122 is cold to the touch, that patient 122 has a runny nose, or that patient 122 has chronic obstructive lung disease (COLD). In other examples, as discussed above, multiple alternative hypotheses for a fact to be extracted from a portion of the text may be identified, e.g., as the text is processed by one or more statistical fact extraction models. In such situations, fact review component 106 in some embodiments may provide a structured choice to the user to disambiguate between multiple facts tentatively extracted by fact extraction component 104. In some embodiments, each of the options provided in the structured choice may correspond to one of the multiple tentative facts, and the user may choose one of the options to specify which fact should actually be extracted from the free-form narration. As discussed above, if the user choosing among the facts is a person other than clinician 120, such as coding specialist 150, then in some embodiments clinician 120 may be prompted to approve the user's choice before finally approving the set of facts for the patient encounter. In other embodiments, the user may be prompted to provide disambiguating information in free-form, rather than as a structured choice, as aspects of the present disclosure relating to prompting for disambiguating information are not limited to any particular implementation.

In various situations, as discussed above, fact review component 106 may be programmed to generate an alert including a structured choice among a number of options corresponding to medical facts that could possibly be ascertained from the patient encounter. Such a structured choice could include a choice among facts that could add specificity to a set of clinical facts already collected for the patient encounter, a choice among facts potentially implied by one or more combinations of facts already collected for the patient encounter, a choice to disambiguate between facts, or any other choice in which one or more structured options are presented to the user, from which the user may choose. Such a structured choice may be provided in any suitable way, including as a visual and/or audio listing of the options in the structured choice, as aspects of the present disclosure are not limited in this respect. Similarly, the user's selection of an option from the structured choice may be received in any suitable way, including as manual input and/or spoken input, as aspects of the present disclosure are not limited in this respect.

In some embodiments, in response to the user's selection of one of the options, fact review component 106 may, for example through use of fact extraction component 104, perform an update to the text narrative to make it explicitly state information corresponding to the selected fact. For example, in some embodiments, fact extraction component 104 may in a sense work backward from the selected fact to generate natural language text from which that fact could have been extracted in the forward sense. In some embodiments, the generated text may then be added to the text narrative. When the fact selected by the user through the structured choice is a replacement for or a disambiguation of a fact already extracted from the text narrative, the generated text may in some embodiments be used to replace the portion of the text narrative from which the original fact was extracted. In some embodiments, to determine where in the text narrative to add the generated text when no other text is to be replaced, fact extraction component 104 may again work backward based on how the selected fact would have been extracted from the narrative. For example, in some embodiments fact extraction component 104 may identify a section heading in the text narrative corresponding to the selected fact, and the generated text may be added to that section. (e.g., because a selected fact with a status of "history" would have been extracted from a section with a "history" heading, the corresponding generated text may be added to such a section in the text narrative.) In other embodiments, generated text may simply be added to a predetermined location in the text narrative, such as at the beginning or end of the narrative, regardless of the semantic content of the generated text.

In some embodiments, fact review component 106 may allow the user to specify a location in the text narrative where the generated text should be inserted, or may allow the user to correct the location initially determined automatically. In some embodiments, fact extraction component 104 or another suitable component may be used to update the generated text in response to the user's indication of a new location at which to insert it in the text narrative. For example, based on whether the user selects a location that is sentence-initial, sentence-medial or sentence-final, or a location that is its own sentence or is within another sentence, the generated text may be adjusted in terms of capitalization, spacing, punctuation, etc., to fit the selected location syntactically. In another example, if a selected fact specifies a family history of a certain condition, the gender of one or more pronouns within the generated text may be adjusted based on whether the user selects a location in a sentence about a female relative or about a male relative. As in other situations, if the user selecting an option from a structured choice and/or specifying a location in the text narrative is a person other than clinician 120, in some embodiments clinician 120 may be prompted to approve the user's selections prior to finally approving the set of clinical facts.

Figure 12:
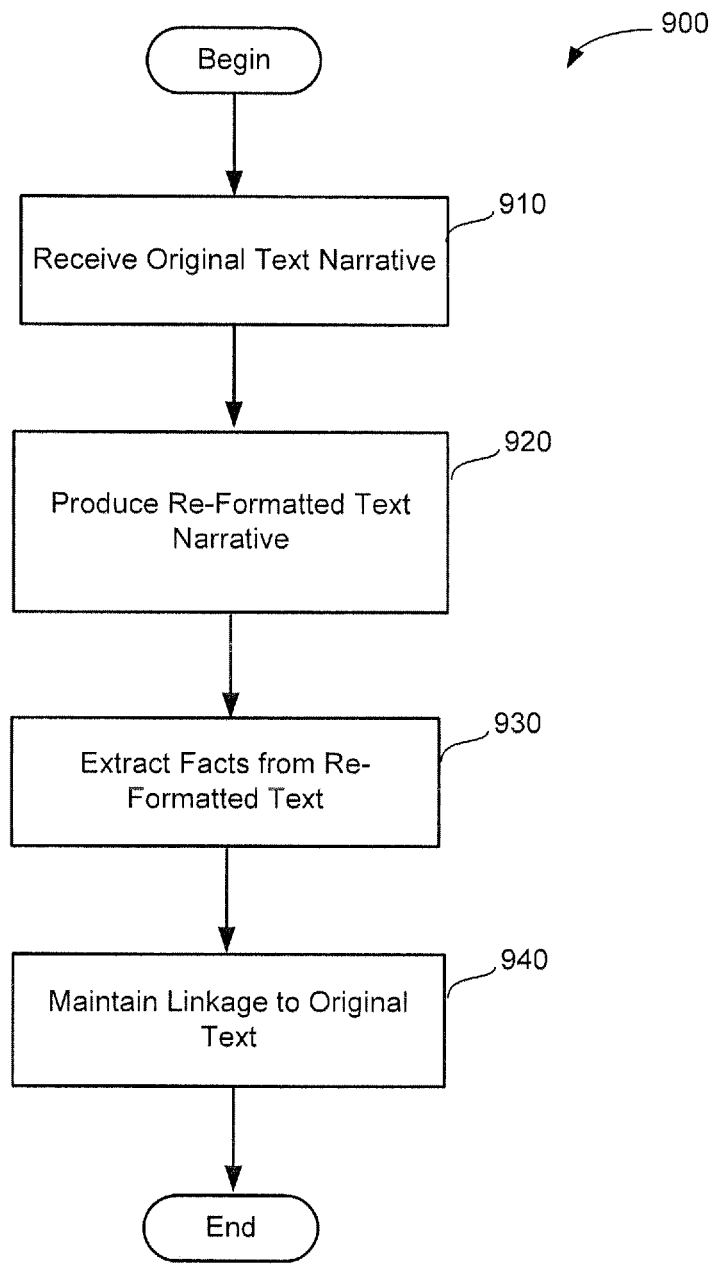
FIG. 12 shows an illustrative method for formatting text for clinical fact extraction, in accordance with some embodiments.

It should be appreciated from the foregoing that another embodiment of the present disclosure is directed to a method 900 for formatting text for clinical fact extraction, as illustrated in FIG. 12. Method 900 may be performed, for example, by one or more components of a fact review system such as ASR engine 102 and/or fact extraction component 104, although other implementations are possible as method 900 is not limited in this respect. Method 900 begins at act 910, at which an original text narrative (e.g., a textual representation of a narration of a patient encounter provided by a clinician) may be received. At act 920, the original text may be re-formatted to produce a formatted text narrative. At act 930, one or more clinical facts may be extracted from the formatted text. Method 900 ends at act 940, at which a linkage between at least one of the clinical facts and a corresponding portion of the original text may be maintained.

Figure 13:
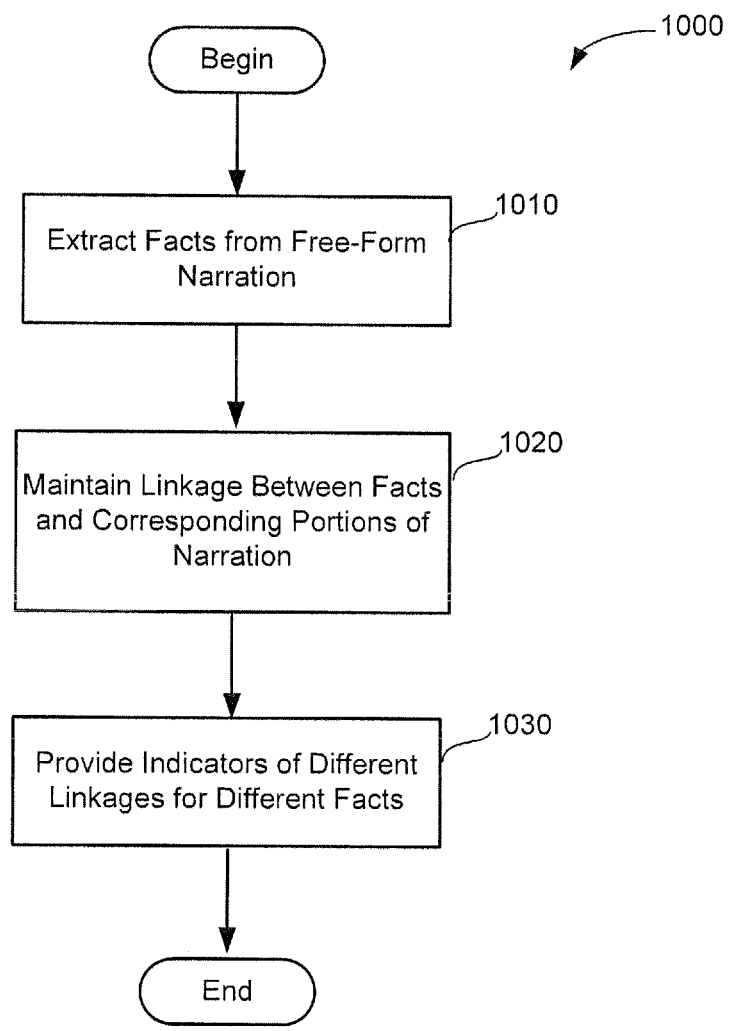
FIG. 13 shows an illustrative method for linking extracted clinical facts to text, in accordance with some embodiments.

It should be appreciated from the foregoing that another embodiment of the present disclosure is directed to a method 1000 for linking extracted clinical facts to text, as illustrated in FIG. 13. Method 1000 may be performed, for example, by one or more components of a fact review system such as fact extraction component 104 and/or fact review component 106, although other implementations are possible and method 1000 is not limited in this respect. Method 1000 begins at act 1010, at which a plurality of facts may be extracted from a free-form narration of a patient encounter provided by a clinician. At act 1020, a linkage may be maintained between each fact (or at least two of the facts) and the corresponding portion of the free-form narration from which it was extracted. Method 1000 ends at act 1030, at which a different indicator may be provided for each fact, to indicate the linkage between that fact and its corresponding portion of the free-form narration.

Figure 14:
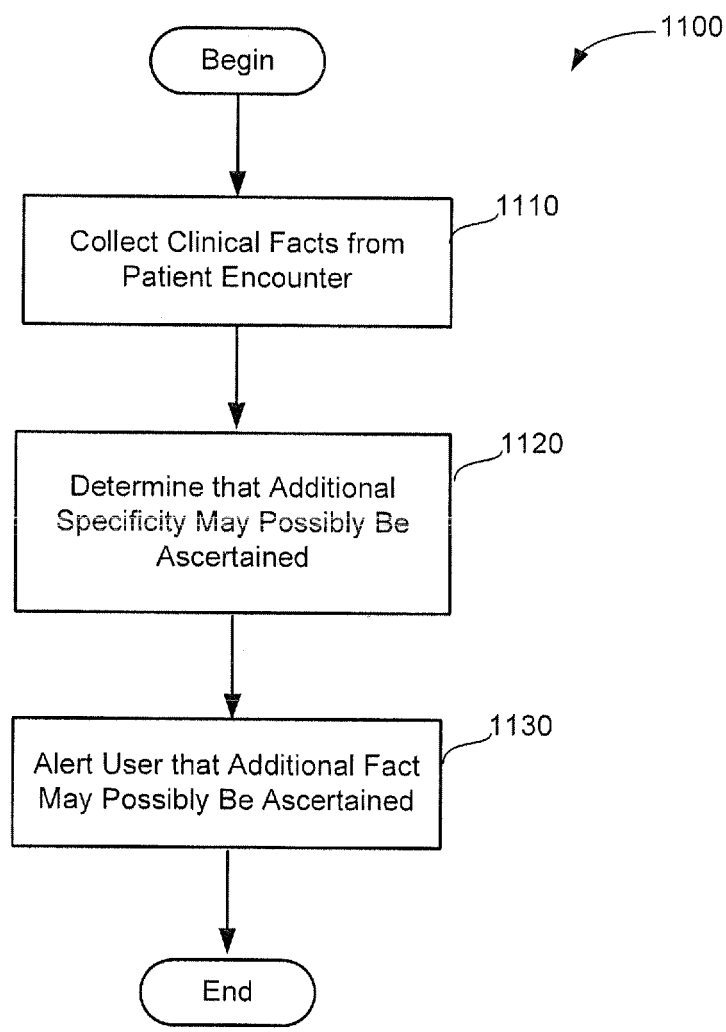
FIG. 14 shows an illustrative method for analyzing specificity, in accordance with some embodiments.

It should be appreciated from the foregoing that another embodiment of the present disclosure is directed to a method 1100 for analyzing specificity in clinical documentation, as illustrated in FIG. 14. Method 1100 may be performed, for example, by one or more components of a fact review system such as ASR engine 102, fact extraction component 104 and/or fact review component 106, although other implementations are possible and method 1100 is not limited in this respect. Method 1100 begins at act 1110, at which a set of one or more clinical facts may be collected from a clinician's encounter with a patient. At act 1120, it may be determined from the set of facts that additional specificity may possibly be ascertained from the patient encounter. Method 1100 ends at act 1130, at which a user may be alerted that an additional fact adding specificity to the set of facts may possibly be ascertained from the patient encounter.

Figure 15:
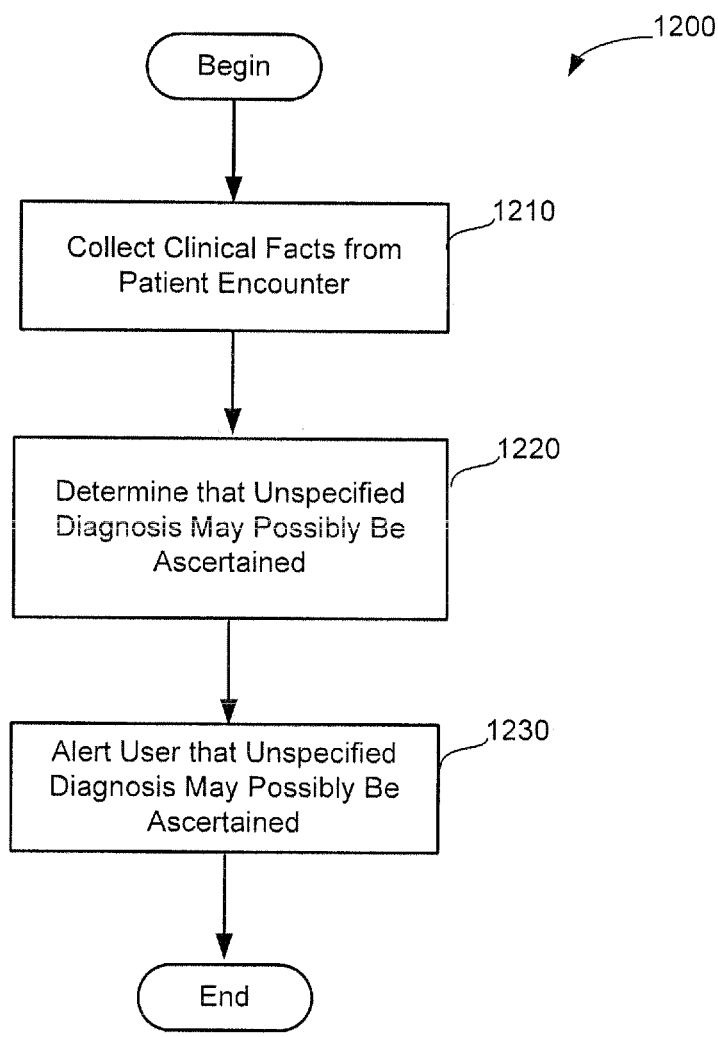
FIG. 15 shows an illustrative method for identifying an unspecified diagnosis, in accordance with some embodiments.

It should be appreciated from the foregoing that another embodiment of the present disclosure is directed to a method 1200 for identifying unspecified diagnoses in clinical documentation, as illustrated in FIG. 15. Method 1200 may be performed, for example, by one or more components of a fact review system such as ASR engine 102, fact extraction component 104 and/or fact review component 106, although other implementations are possible and method 1200 is not limited in this respect. Method 1200 begins at act 1210, at which a set of one or more clinical facts may be collected from a clinician's encounter with a patient. At act 1220, it may be determined from the set of facts that an unspecified diagnosis may possibly be ascertained from the patient encounter. Method 1200 ends at act 1230, at which a user may be alerted that the unspecified diagnosis may possibly be ascertained from the patient encounter.

Figure 16:
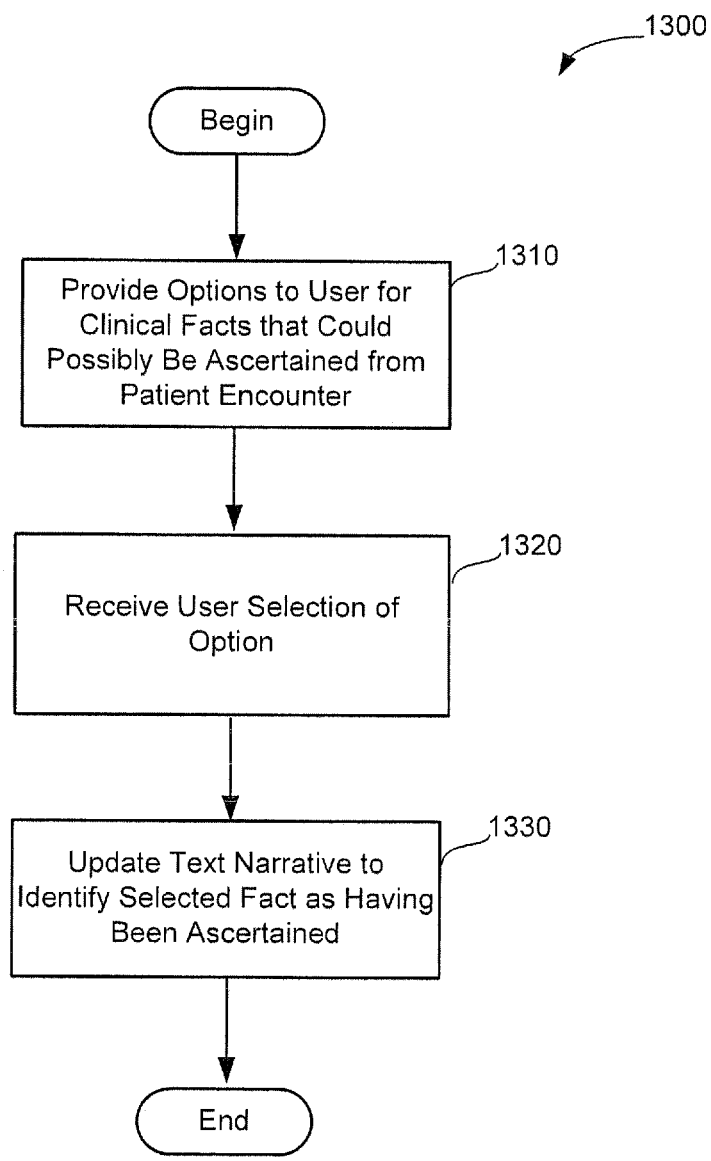
FIG. 16 shows an illustrative method for updating text, in accordance with some embodiments.

It should be appreciated from the foregoing that another embodiment of the present disclosure is directed to a method 1300 for updating text in clinical documentation, as illustrated in FIG. 16. Method 1300 may be performed, for example, by one or more components of a fact review system such as fact extraction component 104 and/or fact review component 106, although other implementations are possible and method 1300 is not limited in this respect. Method 1300 begins at act 1310, at which one or more options may be provided to a user, the one or more options corresponding to one or more clinical facts that could possibly be ascertained from a patient encounter. At act 1320, a user selection of one of the options may be received. Method 1300 ends at act 1330, at which a text narrative (e.g., a textual representation of a free-form narration of the patient encounter provided by a clinician) may be updated to identify the fact corresponding to the selected option as having been ascertained from the patient encounter.

Figure 17:
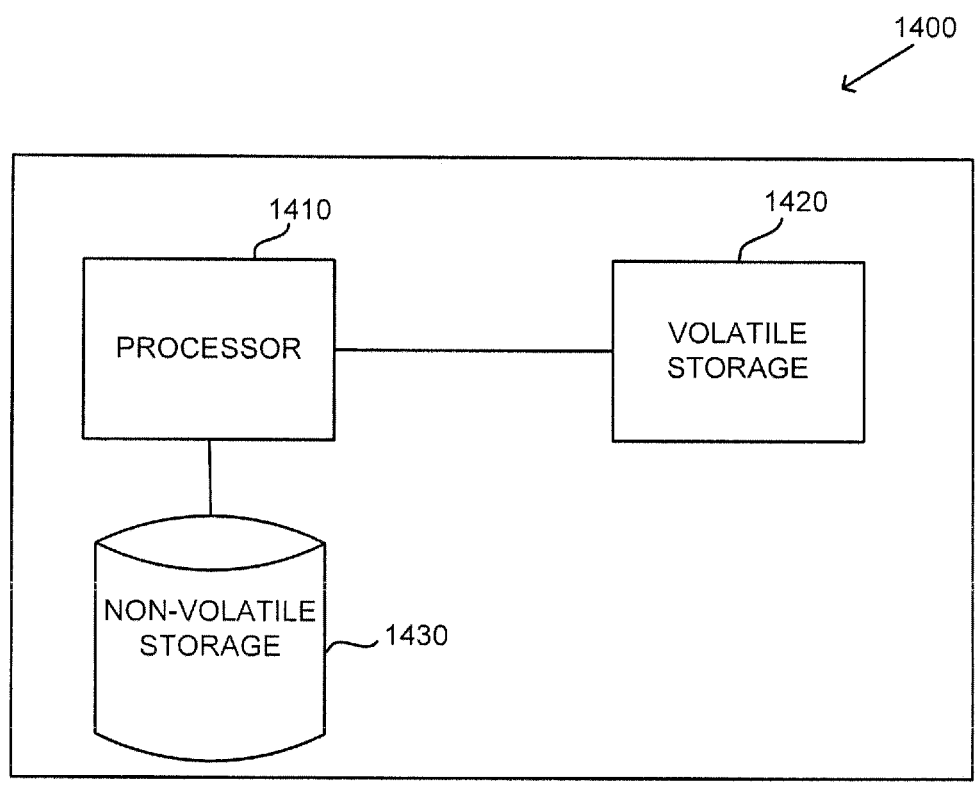
FIG. 17 shows an illustrative computer system on which aspects of the present disclosure may be implemented, in accordance with some embodiments.

A medical documentation system in accordance with the techniques described herein may take any suitable form, as aspects of the present disclosure are not limited in this respect. An illustrative implementation of a computer system 1400 that may be used in connection with some embodiments of the present disclosure is shown in FIG. 17. One or more computer systems such as computer system 1400 may be used to implement any of the functionality described above. The computer system 1400 may include one or more processors 1410 and one or more tangible, non-transitory computer-readable storage media (e.g., volatile storage 1420 and one or more non-volatile storage media 1430, which may be formed of any suitable non-volatile data storage media). The processor 1410 may control writing data to and reading data from the volatile storage 1420 and the non-volatile storage device 1430 in any suitable manner, as the aspects of the present disclosure are not limited in this respect. To perform any of the functionality described herein, the processor 1410 may execute one or more instructions stored in one or more computer-readable storage media (e.g., volatile storage 1420), which may serve as tangible, non-transitory computer-readable storage media storing instructions for execution by the processor 1410.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present disclosure comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present disclosure. The computer-readable storage medium can be transportable such that the program stored thereon can be loaded onto any computer resource to implement aspects of the present disclosure discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present disclosure.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the present disclosure in detail, various modifications and improvements will readily occur to those skilled in the art. Such modifications and improvements are intended to be within the spirit and scope of the present disclosure. Accordingly, the foregoing description is by way of example only, and is not intended as limiting. The present disclosure is limited only as defined by the following claims and the equivalents thereto.

What is claimed is:

1. A system comprising:
   at least one processor; and
   at least one storage medium storing executable instructions that, when executed by the at least one processor, cause the at least one processor to carry out a method comprising:
   analyzing a medical report to determine whether the medical report includes at least one critical finding, wherein a critical finding indicates that content of the medical report indicates a patient is experiencing a medical condition to which an urgent response is warranted, wherein analyzing the medical report comprises acts of:
   applying at least one statistical model, trained to recognize in medical reports text indicative of a critical finding, to at least a first portion of text of the medical report and/or to contextual information associated with the medical report, wherein applying the at least one statistical model comprises:
   tokenizing text of at least the first portion of text of the medical report;
   determining, with the at least one statistical model, a concept related to one or more words and/or phrases of at least the first portion of text of the medical report;
   identifying, with the at least one statistical model, a candidate critical finding from at least the first portion of text of the medical report;
   determining, with the at least one statistical model, a confidence value representing a likelihood that the candidate critical finding is a critical finding; and
   evaluating the confidence value determined for the candidate critical finding using the at least one statistical model to determine whether the candidate critical finding is a critical finding; and
   in response to determining that the medical report includes the at least one critical finding, triggering a notification for at least one medical professional, wherein the notification indicates that the medical report indicates that the patient is experiencing a medical condition to which an urgent response is warranted.

2. The system of claim 1, wherein:
   the contextual information comprises metadata associated with the medical report; and
   applying the at least one statistical model to at least the first portion and/or the contextual information comprises applying the at least one statistical model to at least the first portion and to the metadata associated with the medical report.

3. The system of claim 1, wherein applying the at least one statistical model to at least the first portion and/or the contextual information comprises applying the at least one statistical model to the first portion and to one or more second portions of text from the medical report that are different from the first portion.

4. The system of claim 1, wherein the at least one statistical model is at least one first statistical model and the likelihood is a first likelihood and wherein the method further comprises:
   analyzing the medical report to determine whether the medical report includes at least one instance of at least one type of fact selected from a group consisting of: gender error and laterality error, comprising applying at least one second statistical model, trained to recognize in medical reports text indicative of a gender error and/or a laterality error to the at least the first portion and/or to contextual information to determine a second likelihood that the first portion includes at least one instance of at least one type of fact selected from the group;
   evaluating the second likelihood determined for the first portion using the at least one second statistical model to determine whether the first portion includes at least one instance of at least one type of fact selected from the group; and
   in response to determining that the first portion of the medical report includes at least one instance of a gender error and/or a laterality error, triggering presentation to a user of at least one indication that the first portion of the medical report has been determined to contain the at least one instance of gender error and/or laterality error.

5. The system of claim 4, wherein the method further comprises:
presenting the at least one indication to the user, wherein presenting the at least one indication to the user comprises:
displaying to the user at least a part of the medical report comprising the first portion that was determined to contain the at least one instance of a gender error and/or a laterality error; and
differentiating the first portion of the text from at least one other portion of the text of the medical report to identify the first portion as including the at least one instance of a gender error and/or a laterality error.

6. The system of claim 5, wherein displaying to the user the first portion of the medical report comprises displaying the first portion in response to activation by the user of at least one user interface feature that, when activated by the user, causes at least the first portion of the text of the medical report to be displayed to the user.

7. The system of claim 4, wherein the at least one type of fact is laterality error.

8. The system of claim 4, wherein the at least one type of fact is gender error.

9. The system of claim 4, wherein the method further comprises:
training the at least one first statistical model to recognize text in medical reports indicative of a critical finding and training at least one second statistical model to recognize text in medical reports indicative of a gender error and/or a laterality error, wherein training the at least one first statistical model comprises training the at least one first statistical model with a corpus of medical reports that are each associated with information indicating whether the medical report includes a critical finding and wherein training the at least one second statistical model comprises training the at least one second statistical model with a corpus of medical reports that are each associated with information indicating whether the medical report includes a gender error and/or a laterality error.

10. The system of claim 4, wherein evaluating the first confidence value determined for the candidate critical finding using the at least one first statistical model to determine whether the candidate critical finding is a critical finding and evaluating the second likelihood determined for the first portion using the at least one second statistical model to determine whether the first portion includes at least one instance of at least one type of fact selected from the group comprises determining whether at least one of the confidence value or the second likelihood is above a threshold level.

11. The system of claim 10, wherein determining whether at least one of the first likelihood or the second likelihood is above a threshold level comprises one or more of:
determining whether the first portion includes a gender error by determining whether the second likelihood is above a first threshold;
determining whether the first portion includes a laterality error by determining whether the second likelihood is above a second threshold; or
determining whether the first includes a critical finding by determining whether the confidence value is above a third threshold,
wherein the first threshold, second threshold, and third thresholds have different threshold values.

12. The system of claim 1, wherein evaluating the confidence value determined for the candidate critical finding using the at least one statistical model to determine whether the candidate critical finding is a critical finding comprises evaluating the confidence value using one or more thresholds.

13. The system of claim 12, wherein evaluating the confidence value using the one or more thresholds comprises determining whether the confidence value exceeds at least one threshold of the one or more thresholds.

14. A method comprising:
using at least one processor to analyze a medical report to determine whether the medical report includes at least one critical finding, wherein a critical finding indicates that the medical report indicates that at a time of the medical report the patient is experiencing a condition for which the patient should receive urgent treatment, wherein analyzing the medical report comprises acts of:
applying at least one statistical model, trained to recognize in medical reports text indicative of a critical finding, to at least a first portion of text of the medical report and to contextual information associated with the medical report, wherein applying the at least one statistical model comprises:
tokenizing text of at least the first portion of text of the medical report;
determining, with the at least one statistical model, a concept related to one or more words and/or phrases of at least the first portion of text of the medical report;
identifying, with the at least one statistical model, a candidate critical finding from at least the first portion of text of the medical report;
determining, with the at least one statistical model, a confidence value representing a likelihood that the candidate critical finding is a critical finding; and
evaluating the confidence value determined for the candidate critical finding using the at least one statistical model to determine whether the candidate critical finding is a critical finding; and
in response to determining that the medical report includes the at least one critical finding, triggering presentation of an alert indicating that urgent treatment of the patient may be warranted.

15. The method of claim 14, wherein:
the contextual information comprises metadata associated with the medical report; and
applying the at least one statistical model to at least the first portion and/or the contextual information comprises applying the at least one statistical model to at least the first portion and to the metadata associated with the medical report.

16. The method of claim 14, wherein applying the at least one statistical model to at least the first portion and/or the contextual information comprises applying the at least one statistical model to the first portion and to one or more second portions of text from the medical report that are different from the first portion.

17. The method of claim 14, wherein the at least one statistical model is at least one first statistical model and the likelihood is a first likelihood and wherein the method further comprises:
analyzing the medical report to determine whether the medical report includes at least one instance of at least one type of fact selected from a group consisting of: gender error and laterality error, comprising applying at least one second statistical model, trained to recognize in medical reports text indicative of a gender error and/or a laterality error to the at least the first portion and/or to contextual information to determine a second likelihood that the first portion includes at least one instance of at least one type of fact selected from the group;

evaluating the second likelihood determined for the first portion using the at least one second statistical model to determine whether the first portion includes at least one instance of at least one type of fact selected from the group; and in response to determining that the first portion the medical report includes at least one instance of a gender error and/or a laterality error, triggering presentation to a user of at least one indication that the first portion of the medical report has been determined to contain the at least one instance of gender error and/or laterality error.

18. The method of claim 17, further comprising:

presenting the at least one indication to the user, wherein presenting the at least one indication to the user comprises:

displaying to the user at least a part of the medical report comprising the first portion that was determined to contain the at least one instance of a gender error and/or a laterality error; and differentiating the first portion of the text from at least one other portion of the text of the medical report to identify the first portion as including the at least one instance of a gender error and/or a laterality error.

19. The method of claim 18, wherein displaying to the user the first portion of the medical report comprises displaying the first portion in response to activation by the user of at least one user interface feature that, when activated by the user, causes at least the first portion of the text of the medical report to be displayed to the user.

20. The method of claim 17, wherein the at least one type of fact is laterality error.

21. At least one non-transitory computer-readable storage medium having stored thereon instructions that, when executed by at least one processor, perform a method comprising:

analyzing a medical report regarding a patient to determine whether the medical report includes at least one critical finding, wherein a critical finding indicates that the medical report indicates that the patient is experiencing a critical condition for which a medical professional should be urgently alerted, wherein analyzing the medical report comprises acts of:

applying at least one statistical model, trained to recognize in medical reports text indicative of a critical finding, to at least a first portion of text of the medical report and to contextual information associated with the medical report, wherein applying the at least one statistical model comprises:

tokenizing text of at least the first portion of text of the medical report into syntactic substructure for the text;

determining, with the at least one statistical model, a concept related to one or more words and/or phrases of at least the first portion of text of the medical report;

identifying, with the at least one statistical model, a candidate critical finding from at least the first portion of text of the medical report;

determining, with the at least one statistical model, a confidence value representing a likelihood that candidate critical finding is a critical finding; and evaluating the confidence value determined for the candidate critical finding using the at least one statistical model to determine whether the candidate critical finding is a critical finding; and in response to determining that the medical report includes the at least one critical finding, triggering presentation to at least one medical professional of an alert indicating that the medical report was determined to include the at least one critical finding.

\* \* \* \* \*